US009498260B2

(12) United States Patent
Funk et al.

(10) Patent No.: US 9,498,260 B2
(45) Date of Patent: Nov. 22, 2016

(54) IMPLANTABLE ORTHOPEDIC DEVICE COMPONENT SELECTION INSTRUMENT AND METHODS

(71) Applicant: GLOBUS MEDICAL, INC., Audubon, PA (US)

(72) Inventors: Michael J Funk, North Bend, WA (US); Thomas J McLeer, Redmond, WA (US); Teena M Augostino, King of Prussia, PA (US); Richard J Broman, Kirkland, WA (US); Leonard J Tokish, Jr., Issaquah, WA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 179 days.

(21) Appl. No.: 14/165,122

(22) Filed: Jan. 27, 2014

(65) Prior Publication Data
US 2015/0209088 A1   Jul. 30, 2015

Related U.S. Application Data

(60) Continuation of application No. 12/186,461, filed on Aug. 5, 2008, now Pat. No. 8,675,930, which is a division of application No. 11/236,323, filed on Sep. 26, 2005, now Pat. No. 7,406,775, which is a continuation-in-part of application No. 11/071,541, filed on Mar. 2, 2005, now Pat. No. 7,674,293.

(60) Provisional application No. 60/642,321, filed on Jan. 7, 2005.

(51) Int. Cl.
| A61B 17/88 | (2006.01) |
| A61B 17/70 | (2006.01) |
| A61F 2/44  | (2006.01) |
| A61F 2/46  | (2006.01) |
| A61F 2/30  | (2006.01) |

(52) U.S. Cl.
CPC ......... *A61B 17/7064* (2013.01); *A61F 2/4405* (2013.01); *A61F 2/4657* (2013.01); *A61B 17/7032* (2013.01); *A61F 2/4684* (2013.01);*A61F 2002/3008* (2013.01); *A61F 2002/3021* (2013.01); *A61F 2002/30405* (2013.01); *A61F 2002/30601* (2013.01); *A61F 2002/4658* (2013.01); *A61F 2002/4662* (2013.01); *A61F 2002/4668* (2013.01); *A61F 2220/0025* (2013.01); *A61F 2230/0067* (2013.01); *A61F 2250/0098* (2013.01)

(58) Field of Classification Search
CPC .......... A61B 17/7032; A61B 17/7064; A61F 2/4405; A61F 2/4657; A61F 2/4684; A61F 2002/3008; A61F 2002/3021; A61F 2002/30405; A61F 2002/30601; A61F 2002/4658; A61F 2002/4662; A61F 2002/4668; A61F 2220/0025; A61F 2230/0067; A61F 2250/0098
USPC ............. 606/247, 279, 80, 96, 97, 102, 104, 606/130, 86 A; 33/512
See application file for complete search history.

(56) References Cited

U.S. PATENT DOCUMENTS

| 7,235,076 B2 * | 6/2007 | Pacheco ............. A61B 17/1757 606/53 |
| 2002/0116006 A1 * | 8/2002 | Cohen .................. A61B 17/025 606/99 |
| 2006/0036264 A1 * | 2/2006 | Selover ................ A61B 19/201 606/130 |

*Primary Examiner* — Pedro Philogene
*Assistant Examiner* — David C Comstock

(57) ABSTRACT

The present invention provides tools and methods designed to aid in the placement of artificial facet joints at virtually all spinal levels. One aspect of the present invention is a measurement tool for installing an artificial cephalad facet joint including a fixation measurement element and a support arm element. This measurement tool assists in the selection and/or configuration of an artificial cephalad facet joint for implantation in a patient. Another aspect is a measurement tool for installing a caudad facet joint including a stem element and a trial caudad bearing surface element. This measurement tool assists in the selection and/or configuration of a caudad facet joint for implantation in a patient. Yet another aspect is a measurement tool holder including a measurement surface connected to a holder element. This tool holder assists in determining the measurements obtained with the caudad facet joint measurement tool.

20 Claims, 21 Drawing Sheets

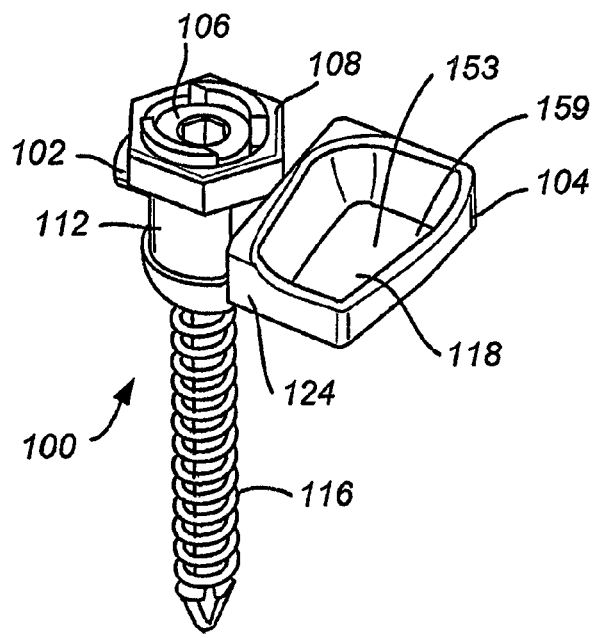
FIG. 9
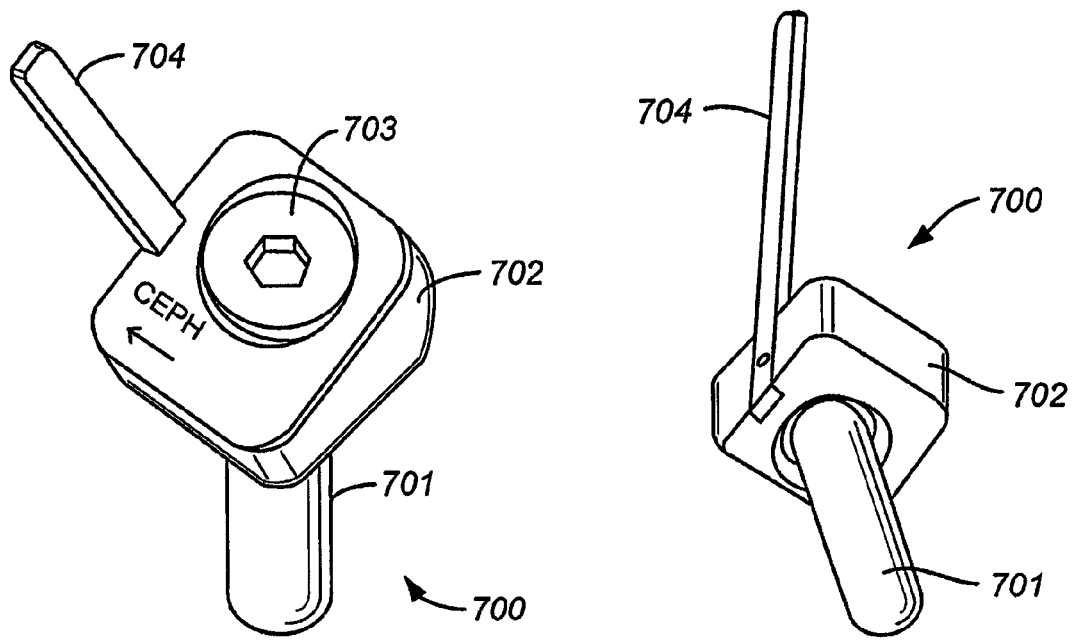
FIG. 10a
FIG. 10b

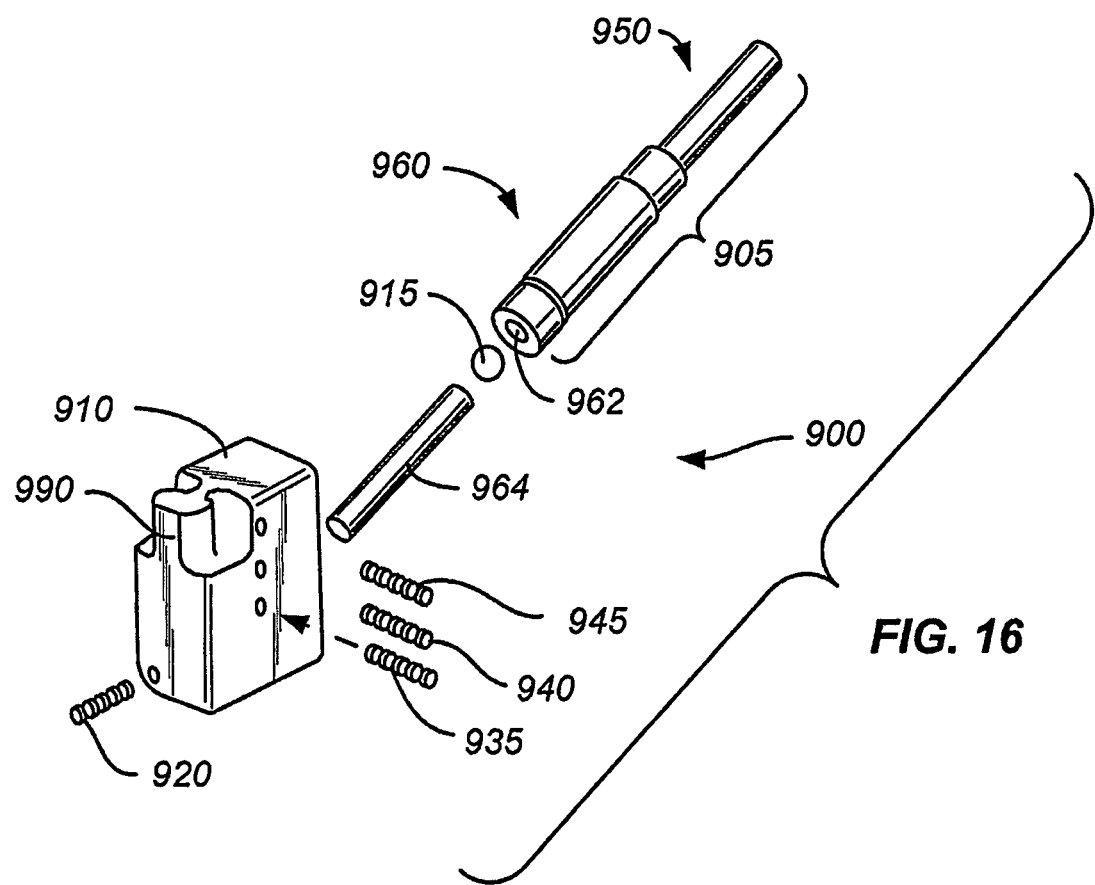

IMPLANTABLE ORTHOPEDIC DEVICE COMPONENT SELECTION INSTRUMENT AND METHODS

CROSS REFERENCE TO RELATED APPLICATIONS

This application is a continuation of U.S. Ser. No. 12/186,461, filed Aug. 5, 2008, entitled "IMPLANTABLE ORTHOPEDIC DEVICE COMPONENT SELECTION INSTRUMENT AND METHODS," which is a divisional of U.S. application Ser. No. 11/236,323 filed on Sep. 26, 2005, now issued as U.S. Pat. No. 7,406,775, entitled, "IMPLANTABLE ORTHOPEDIC DEVICE COMPONENT SELECTION INSTRUMENT AND METHODS," which is a continuation-in-part of commonly assigned U.S. patent application Ser. No. 10/831,651, filed Apr. 22, 2004, now issued as U.S. Pat. No. 7,051,451, and entitled "Facet joint Measurement and Implant Tools," both of which are incorporated herein by reference. The aforementioned U.S. Ser. No. 12/186,461 is also a divisional of U.S. application Ser. No. 11/236,323, filed on Sep. 26, 2005, entitled, "IMPLANTABLE ORTHOPEDIC DEVICE COMPONENT SELECTION INSTRUMENT AND METHODS," which is also a continuation-in-part of commonly assigned U.S. patent application Ser. No. 11/071,541, filed Mar. 2, 2005, now U.S. Pat. No. 7,647,293, and entitled "Crossbar Spinal Prosthesis Having a Modular Design and Related Implantation Methods," which is incorporated herein by reference which in turn claims the benefit of U.S. Provisional Patent Application Ser. No. 60/642,321 to Funk et al, filed Jan. 7, 2005, and entitled "Component Selection Instrument." All of the references cited herein are hereby incorporated by reference in their entireties.

FIELD OF THE INVENTION

This invention relates to implantable spinal devices, systems, and methods for treating various types of spinal pathologies. The invention relates in particular to the sizing and attachment of implantable devices to spinal vertebrae using component selection tools and methods.

BACKGROUND OF THE INVENTION

Back pain, particularly in the small of the back, or lumbosacral region (L4-S1) of the spine, is a common ailment. In many cases, the pain severely limits a person's functional ability and quality of life. Back pain interferes with work, routine daily activities, and recreation. It is estimated that Americans spend $50 billion each year on low back pain alone. It is the most common cause of job-related disability and a leading contributor to missed work.

Through disease or injury, the laminae, spinous process, articular processes, facets and/or facet capsule(s) of one or more vertebral bodies along with one or more intervertebral discs can become damaged which can result in a loss of proper alignment or loss of proper articulation of the vertebra. This damage can result in anatomical changes, loss of mobility, and pain or discomfort. For example, the vertebral facet joints can be damaged by traumatic injury or as a result of disease. Diseases damaging the spine and/or facets include osteoarthritis where the cartilage of joint is gradually worn away and the adjacent bone is remodeled, ankylosing spondylolysis (or rheumatoid arthritis) of the spine which can lead to spinal rigidity, and degenerative spondylolisthesis which results in a forward displacement of the lumbar vertebra on the sacrum. Damage to facet joints of the vertebral body often can also results in pressure on nerves, commonly referred to as "pinched" nerves, or nerve compression or impingement. The result is pain, misaligned anatomy, and a corresponding loss of mobility. Pressure on nerves can also occur without facet joint pathology, e.g., a herniated disc.

One conventional treatment of facet joint pathology is spine stabilization, also known as intervertebral stabilization. Intervertebral stabilization desirably controls, prevents or limits relative motion between the vertebrae, through the use of spinal hardware, removal of some or all of the intervertebral disc, fixation of the facet joints, bone graft/osteo-inductive /osteo-conductive material (with or without concurrent insertion of fusion cages) positioned between the vertebral bodies, and/or some combination thereof, resulting in the fixation of (or limiting the motion of) any number of adjacent vertebrae to stabilize and prevent/limit/control relative movement between those treated vertebrae. Stabilization of vertebral bodies can range from the insertion of motion limiting devices (such as intervertebral spacers, artificial ligaments and/or dynamic stabilization devices), through devices promoting arthrodesis (rod and screw systems, cable fixation systems, fusion cages, etc.), up to and including complete removal of some or all of a vertebral body from the spinal column (which may be due to extensive bone damage and/or tumorous growth inside the bone) and insertion of a vertebral body replacement (generally anchored into the adjacent upper and lower vertebral bodies). Various devices are known for fixing the spine and/or sacral bone adjacent the vertebra, as well as attaching devices used for fixation, including: U.S. Pat. Nos. 6,811,567, 6,619,091, 6,290,703, 5,782,833, 5,738,585, 6,547,790, 6,638,321, 6,520,963, 6,074,391, 5,569,247, 5,891,145, 6,090,111, 6,451,021, 5,683,392, 5,863,293, 5,964,760, 6,010,503, 6,019,759, 6,540,749, 6,077,262, 6,248,105, 6,524,315, 5,797,911, 5,879,350, 5,885,285, 5,643,263, 6,565,565, 5,725,527, 6,471,705, 6,554,843, 5,575,792, 5,688,274, 5,690,6306, 022,3504, 805,6025, 474,5554, 611, 581, 5,129,900, 5,741,255, 6,132,430: and U.S. Patent Publication No. 2002/0120272.

SUMMARY OF THE INVENTION

What is needed are methods and tools for facilitating the sizing, orientation and implant of implantable spinal devices such as artificial facet joints. Moreover, there is a need in the art for methods and devices which facilitate the less-invasive, minimally-invasive and/or non-invasive measurement of the anatomical characteristics (including size, shape, orientation and/or relationship) of anatomical features of bones such as the vertebrae. The present invention provides tools and methods designed to aid in the placement of implantable facet joints at virtually all spinal levels including, but not limited to, L1-L2, L2-L3, L3-L4, L4-L5, L5-S1, T11-T12, and T12-L1.

Because the specific features of a patient's spinal anatomy can vary significantly from patient to patient (and can also vary within the various spinal levels of an individual patient or even vary between the facet joints in a single vertebral level), an implantable spinal device suitable for implantation into a patient will desirably be configured or tailored to be patient specific in order to accommodate the specific features of that patient's spinal anatomy. For example, the size, spacing and orientation of the pedicles, lamina and associated spinal anatomy, as well as the size, spacing and orientation of the individual facet joints to be replaced, can vary widely depending upon the level and/or patient to be treated.

In order to accommodate such variations in anatomy, a configurable and/or modular implantable device system (comprising multiple configurable and/or interchangeable components of varying shapes and/or sizes) may be used to tailor the implantable device to the varying anatomical demands of a given patient. Once the surgical site has been prepared, the implantable device can be assembled and/or configured from components chosen by the physician based on anatomical measurements of the treatment site during the surgery. The disclosed invention desirably facilitates such measurements of the treated anatomy.

In one aspect, the present invention provides a measurement tool for configuring and installing a cephalad facet joint implantable device including a fixation measurement element and a support arm element. This measurement tool assists in the selection of a cephalad facet joint implantable device for implantation in a patient. The measurement tool can be used in the determination of the dimensions of a cephalad facet joint implantable device. Particularly, this measurement tool can be used to determine the length of the fixation element and support arm element of the cephalad facet joint implantable device.

In some embodiments, the connection between the fixation measurement element and support arm element is a polyaxially adjustable connection. In one embodiment, the fixation measurement element has indentations which control the vertical movement of the support arm element. The indentations on the fixation measurement element can also permit the determination of the length of the fixation element of a cephalad facet joint implantable device.

In one embodiment, the support arm element supports a trial facet joint bearing surface. The bearing surface is intended to predict the location of the facet joint bearing surface of an actual implantable device intended for implantation in a patient.

The fixation measurement element in one embodiment is adapted and configured to permit measurements for determination of the length of the fixation element of a cephalad facet joint implantable device for implantation in a patient. In another embodiment, the fixation measurement element includes markings to assist in the determination of the length of the fixation element of a cephalad facet joint implantable device.

In another aspect, the present invention provides a caudad facet joint implantable device measurement system including a stem element and a trial caudad bearing surface element connected to each other by a fastener or fastening mechanism. This measurement tool assists in the selection of a caudad facet joint implantable device for implantation in a patient. The measurement tool can be used in the determination of the dimensions of a caudad facet joint implantable device. Particularly, this measurement tool can be used to determine the length of the fixation element of the caudad facet joint implantable device to be implanted in a patient. Also, this tool can be used to determine the angle between the artificial facet joint element and fixation element of the caudad facet joint implantable device. If desired, the mechanism can permit motion between the elements for alignment purposes and also allow locking of the chosen configuration/orientation once determined.

In one embodiment, the fastener used in the caudad facet joint implantable device measurement tool is a screw. Examples of other suitable fasteners could include sterns, posts, threads, polyaxial mechanisms, splines, tapers, press fits, bayonet, cap screws, ball detents, friction fits, cams, collets and/or clamps. In certain embodiments, the fastener permits vertical movement of the trial caudad bearing surface element along the stem element. In other embodiments, the fastener permits rotation of the trial caudad bearing surface element in different planes with respect to the stem element. These planes can include movement along the axial and median planes.

In another embodiment, the stem element is adapted and configured to permit measurement of the length of a fixation element of a caudad facet joint implantable device to be implanted in a patient. In yet another embodiment, the stem element of the measurement tool includes markings to permit the measurement of the length of the fixation element.

In one of the embodiments, the measurement tool for the caudad facet joint implantable device is adapted and configured to permit measurement of the angle between the artificial facet joint element and fixation element of a caudad facet joint implantable device to be implanted in a patient. The angle measurements can include measurements in the median, horizontal and frontal planes (such measurements could also include measurements relative to the coronal, sagittal and/or axial planes, if desired). In one embodiment, to facilitate the determination of the angle measurement, the trial caudad bearing surface element is adapted and configured to interact with a measurement tool holder.

In one aspect, the invention is a measurement tool holder including a measurement surface connected to a holder element. This tool holder assists in determining the angle measurements obtained with the caudad facet joint implantable device measurement tool. The caudad facet joint implantable device measurement tool can be placed in the tool holder and the angle between the artificial facet joint element and fixation element of a caudad facet joint implantable device can be determined.

In one embodiment, the measurement tool holder is adapted and configured to hold the measurement tool for the caudad facet joint implantable device. In yet another embodiment, the measurement surface of the tool holder includes two plates at right angles to each other. The plates can include markings to permit determination of the angle measurements, preferably in the horizontal and median planes.

Another aspect of the invention provides a method for determining the dimensions of a cephalad facet joint implantable device to be implanted in a patient. The method includes the steps of forming a hole at a location in the vertebra and placing a fixation measurement element of a cephalad facet joint implantable device measurement tool into the hole. Further optional steps include the steps of obtaining a first length measurement to determine length of a fixation element of a cephalad facet joint implantable device to be implanted in a patient; and obtaining a second length measurement for determining the length of a support arm element of the cephalad facet joint implantable device. In various embodiment, the measurement tool can be used in conjunction with a caudad implantable device or other implanted device, or can be used in conjunction with the caudad joint surface or other natural anatomical landmark.

Yet another aspect of the invention provides a method for determining the dimensions of a caudad facet joint implantable device to be implanted in a patient. The method includes the steps of forming a hole at a location in the vertebra and placing a caudad facet joint implantable device measurement tool into the hole. Further optional steps include the steps of obtaining a length measurement which indicates the length of a fixation element of a caudad facet joint implantable device to be implanted in a patient; and obtaining an angle measurement which indicates the angle between an artificial facet joint element and a fixation element of the caudad facet joint implantable device. In an alternate embodiment, the external surfaces of the measurement tool could incorporate calibrated markings allowing angle measurements to be determined without an associated measurement fixture.

In yet another aspect of the invention a component selection instrument is provided that facilitates the less-invasive, minimally-invasive and/or non-invasive measurement of the anatomical characteristics of the drill channel created in the pedicle in anticipation of implantation of a facet joint implantable device. In the various embodiments, the components of the component selection instrument can be visualized using non-invasive visualization (such as fluoroscopy, etc.) to determine the various appropriate components of a modular facet replacement system without requiring actual trialing of the components prior to permanent implantation.

The invention also includes a component selection tool adapted and configured for use in a spinal column comprising: a stem; a head; and a first marker having a first two dimensional geometric profile at a first location within the component selection tool and a second marker having a second two-dimensional geometric profile at a second location within the component selection tool. In some embodiments, the stem and head of the component selection tool are integrally formed. In other embodiments, the stem and head are component parts and the stem is adapted and configured to engage the head. In yet other embodiments, at least one of the stem and the head are formed from radiolucent material. The first marker can be configured as a radiopaque ball. In contrast, the second radiopaque marker can be configured as a cylindrical rod or tube with a shaped exterior surface. Suitable exterior shapes for the rod include smooth, turned, notched, and etched. Moreover, in other embodiments, a plurality of second radiopaque markers can be provided to provide additional reference markings. In embodiments where a plurality of second radiopaque markers are used, each of the markers can have the same or different shapes which are selected from smooth, turned and notched. In at least some embodiments, the plurality of second radiopaque markers can be configured to lie within a single plane within the component selection tool and can further be configured to be parallel one another within the plane. In at least some embodiments, the second radiopaque marker(s) are located within the head of the component selection tool. Other embodiments of the invention can be configured to provide a third radiopaque marker. The third radiopaque marker can be positioned in a plane that is perpendicular to the plane in which the second radiopaque markers lie. As with the second radiopaque markers, more than one third radiopaque marker can be provided, each or any of which can have an exterior shape that is smooth, turned or notched. Additionally, the third radiopaque marker(s) can be positioned within the head of the component selection tool. Where second and third radiopaque markers are used, the second markers can be configured with a first exterior shape and the third markers can be configured with a second exterior shape to assist in assessing the position of the component selection instrument relative to the anatomy. The third radiopaque markers can also lie parallel one another within the plane or be positioned non-parallel. The stem of the component selection tool can be configured to be telescoping, and can be configured to have a first diameter at a distal end and a second diameter at a proximal end. The first radiopaque marker can be positioned within the stem either integrally or located within a hollow shaft of the stem.

The invention also includes a pair of component selection tools adapted and configured for use in a right and left side of a vertebral body of a spinal column or a first and second vertebral body, each component selection tool comprising: a stem; a head; and a first marker having a first two dimensional geometric profile at a first location within the component selection tool and a second marker having a second two-dimensional geometric profile at a second location within the component selection tool wherein the second marker in a first component selection tool has a first shape and the second marker in a second component selection tool has a second shape different than the first shape of the first component selector tool markers. In some embodiments the shape of the first and second, second radiopaque markers can have the same or different shapes which are selected from smooth, turned, notched and etched. In some embodiments, the stem and head of the component selection tool are integrally formed. In other embodiments, the stem and head are component parts and the stem is adapted and configured to engage the head. In yet other embodiments, at least one of the stem and the head are formed from radiolucent material. In at least some embodiments, the plurality of second radiopaque markers of either of the first or second component selection tool can be configured to lie within a single plane within the component selection tool and can further be configured to be parallel one another within the plane. In at least some embodiments, the second radiopaque marker(s) of either of the first or second component selection tools are located within the head of the component selection tool. Other embodiments of the invention can be configured to provide a third radiopaque marker. The third radiopaque marker for each of the component selection instruments can be positioned in a plane that is perpendicular to the plane in which the second radiopaque markers lie. As with the second radiopaque markers, more than one third radiopaque marker can be provided, each or any of which can have an exterior shape that is smooth, turned or notched. Additionally, the third radiopaque marker(s) can be positioned within the head of the component selection tool. The third radiopaque markers can also lie parallel one another within the plane or be positioned non-parallel. The stem of the component selection tool can be configured to be telescoping, and can be configured to have a first diameter at a distal end and a second diameter at a proximal end. The first radiopaque marker can be positioned within the stem either integrally or located within a hollow shaft of the stem.

Embodiments of the invention also include methods of using a component selection tool comprising: accessing a target anatomy; creating a pilot hole within a portion of the target anatomy; inserting a stem of a component selection tool within the pilot hole; taking a first image of the target anatomy having the component selection tool; analyzing the image of the target anatomy with the component selection tool to determine position of a first marker and a second marker; and selecting a component for implantation into the target anatomy. Templates can be used in combination with the image to analyze the image of the target anatomy with the component selection tool. Further, the pilot hole can be revised to achieve a larger diameter. Thereafter the component selection tool can be placed within the revised pilot hole before taking a second image of the component selection tool in the revised pilot hole.

Embodiments of the invention also include the use of kits, such as a kit comprising a first component selection instrument having a first marker and at least one second marker and a second component selection instrument having a first marker and at least one second marker, wherein the geometric profile of the second marker in the first component selection instrument is not the same as the geometric profile of the second marker in the second component selection instrument.

Embodiments of the invention also include methods, such as a method of using a component selection tool comprising: accessing a target anatomy; creating a pilot hole within a portion of the target anatomy; inserting a stem of a component selection tool within the pilot hole; taking a first image of the target anatomy having the component selection tool; analyzing the image of the target anatomy with the component selection tool to determine position of a first marker and a second marker; and selecting a component for implantation into the target anatomy.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9 is a perspective view of one embodiment of a caudad implantable device for replacing the superior half of a natural facet joint on an inferior vertebral body;

FIGS. 10A and 10B are views of one embodiment of a measurement tool for implanting an artificial caudad facet joint;

FIG. 16 is an exploded view of an alternative embodiment of a measurement tool according to the invention;

DETAILED DESCRIPTION OF THE INVENTION

The invention relates to tools for use with implantable devices, including implantable prosthesis suitable for implantation within the body to restore and/or augment connective tissue such as bone, and systems and methods for treating spinal pathologies that incorporate use of the tools. The invention relates generally to implantable devices and tools for use with implantable devices and apparatuses or mechanisms that are suitable for implantation within a human body to restore, augment, and/or replace soft tissue and connective tissue, including bone and cartilage, and systems for treating spinal pathologies. In various embodiments, the implantable devices used with the tools can include devices designed to replace missing, removed or resected body parts or structure. The implantable devices, tools, apparatus or mechanisms are configured such that the devices or tools can be formed from parts, elements or components which alone, or in combination, comprise the device or tools. Thus, for example the tools can be configured to work with implantable devices formed from parts, elements or components. The implantable devices can also be configured such that one or more elements or components are formed integrally to achieve a desired physiological, operational or functional result such that the components complete the device. Similarly, tools can be configured such that one or more elements or components are formed integrally to achieve a desired physiological, operational or functional result such that the components complete the tool. Functional results can include the surgical restoration and functional power of a joint, controlling, limiting or altering the functional power of a joint, and/or eliminating the functional power of a joint by preventing joint motion. Portions of the device can be configured to replace or augment existing anatomy and/or implanted devices, and/or be used in combination with resection or removal of existing anatomical structure.

Figure 1:
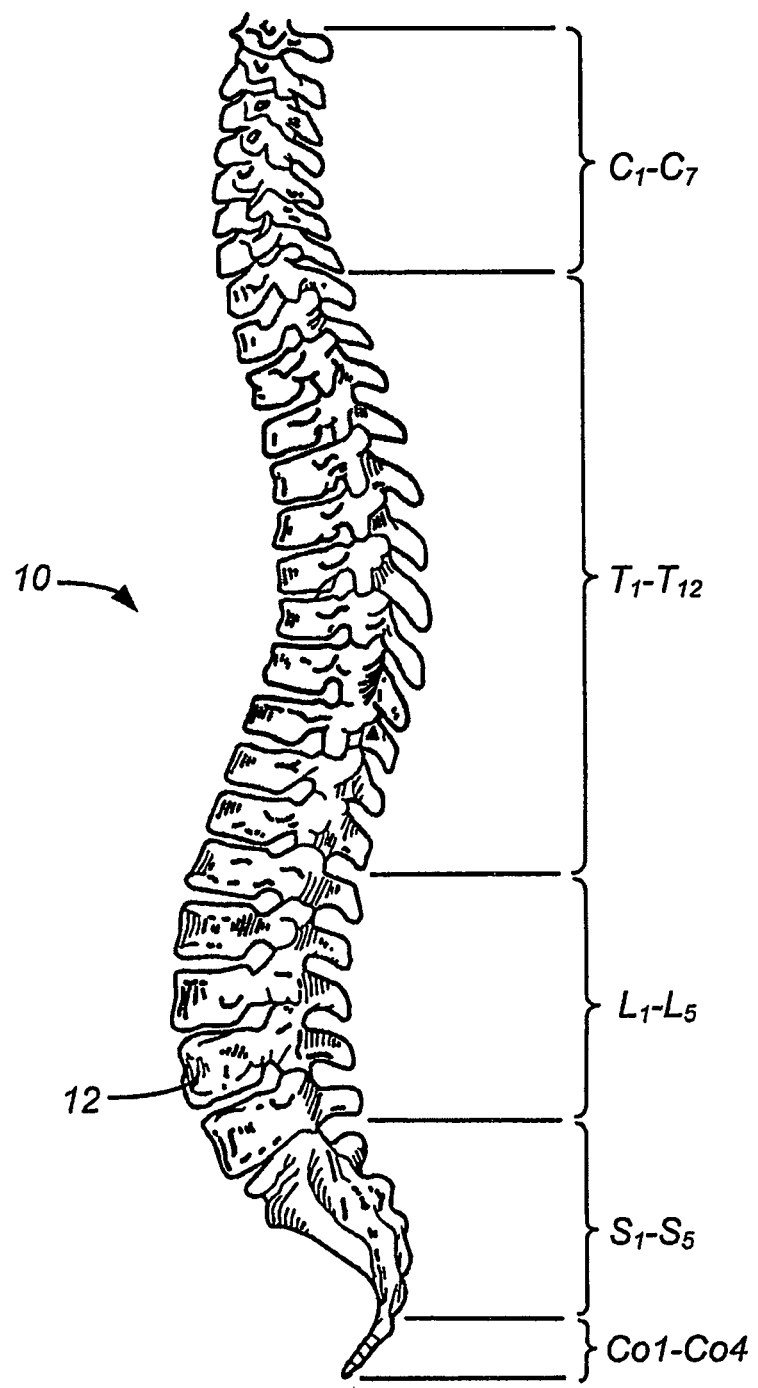
FIG. 1 is a lateral view of a normal human spinal column.

The tools of the invention are designed to interact with the human spinal column 10, as shown in FIG. 1, which is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4.

Figure 2:
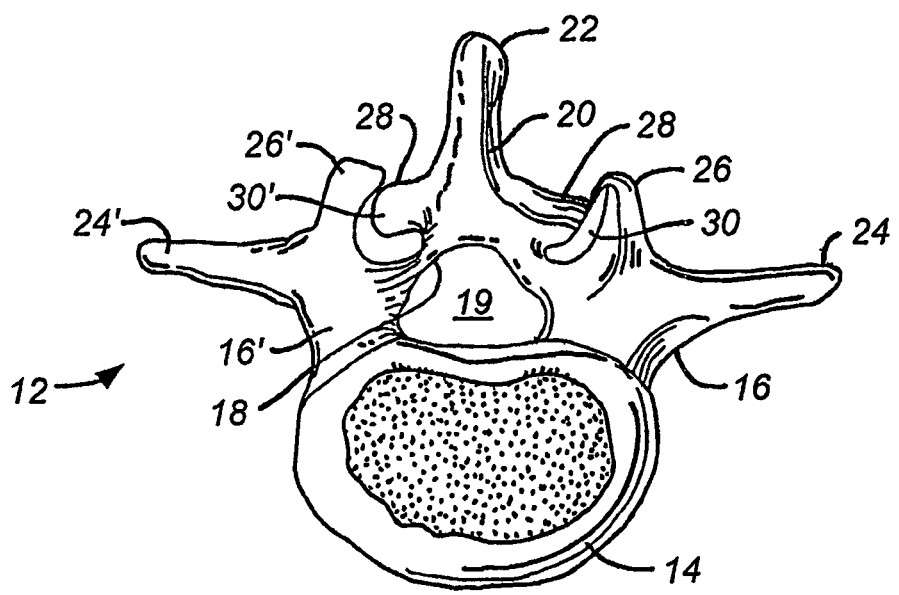
FIG. 2 is a superior view of a normal human lumbar vertebra.

An example of one vertebra is illustrated in FIG. 2 which depicts a superior plan view of a normal human lumbar vertebra 12. Although human lumbar vertebrae vary somewhat according to location, the vertebrae share many common features. Each vertebra 12 includes a vertebral body 14. Two short boney protrusions, the pedicles 16, 16', extend dorsally from each side of the vertebral body 14 to form a vertebral arch 18 which defines the vertebral foramen.

At the posterior end of each pedicle 16, the vertebral arch 18 flares out into broad plates of bone known as the laminae 20. The laminae 20 fuse with each other to form a spinous process 22. The spinous process 22 provides for muscle and ligamentous attachment. A smooth transition from the pedicles 16 to the laminae 20 is interrupted by the formation of a series of processes. Two transverse processes 24, 24' thrust out laterally, one on each side, from the junction of the pedicle 16 with the lamina 20. The transverse processes 24,24' serve as levers for the attachment of muscles to the vertebrae 12. Four articular processes, two superior 26, 26' and two inferior 28, 28', also rise from the junctions of the pedicles 16 and the laminae 20. The superior articular processes 26, 26' are sharp oval plates of bone rising upward on each side of the vertebrae, while the inferior processes 28, 28' are oval plates of bone that jut downward on each side. See also FIG. 4.

Figure 3:
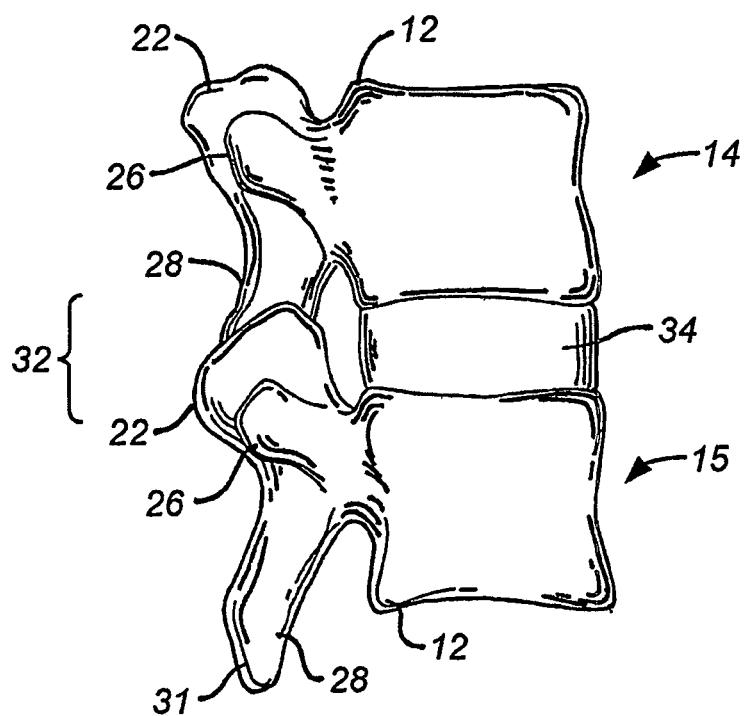
FIG. 3 is a lateral view of a functional spinal unit.

The superior and inferior articular processes 26 and 28 each have a natural bony structure known as a facet. The superior articular facet 30 faces medially upward, while the inferior articular facet 31 (see FIG. 3) faces laterally downward. When adjacent vertebrae 12 are aligned, the facets 30 and 31, capped with a smooth articular cartilage and encapsulated by ligaments, interlock to form a facet joint 32. The facet joints are apophyseal joints that have a loose capsule and a synovial lining.

Figure 4:
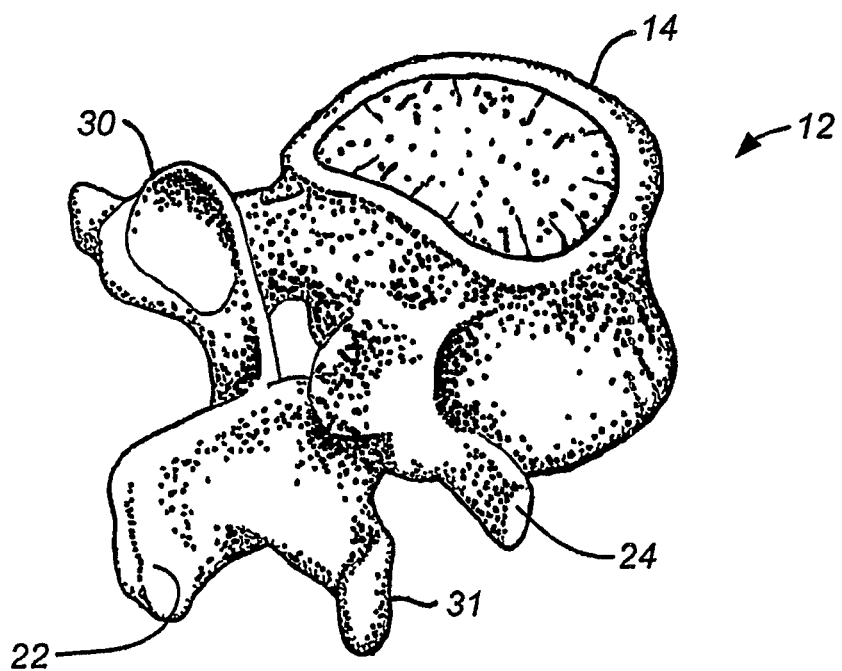
FIG. 4 is a postero-lateral oblique view of a vertebrae.

As discussed, the facet joint 32 is composed of a superior facet 30 and an inferior facet 31 (shown in FIG. 4). The superior facet is formed by the vertebral level below the joint 32, and the inferior facet is formed in the vertebral level above the joint 32. For example, in the L4-L5 facet joint shown in FIG. 3, the superior facet of the joint 32 is formed by bony structure on the L5 vertebra (i.e., a superior articular surface and supporting bone 26 on the L5 vertebra), and the inferior facet of the joint 32 is formed by bony structure on the L4 vertebra (i.e., an inferior articular surface and supporting bone 28 on the L4 vertebra). The angle formed by a facet joint located between a superior facet and an inferior facet changes with respect to the midline of the spine depending upon the location of the vertebral body along the spine. The facet joints do not, in and of themselves, substantially support axial loads unless the spine is in an extension posture (lordosis). As would be appreciated by those of skill in the art, the orientation of the facet joint for a particular pair of vertebral bodies changes significantly from the thoracic to the lumbar spine to accommodate a joint's ability to resist flexion-extension, lateral bending, and rotation.

An intervertebral disc 34 between each adjacent vertebra 12 (with stacked vertebral bodies shown as 14, 15 in FIG. 3) permits gliding movement between the vertebrae 12. The structure and alignment of the vertebrae 12 thus permit a range of movement of the vertebrae 12 relative to each other.

FIG. 4 illustrates a posterolateral oblique view of a vertebrae 12, further illustrating the curved surface of the superior articular facet 30 and the protruding structure of the inferior facet 31 adapted to mate with the opposing superior articular facet. As discussed above, the position of the inferior facet 31 and superior facet 30 varies on a particular vertebral body to achieve the desired biomechanical behavior of a region of the spine.

Thus, the overall spine comprises a series of functional spinal units that are a motion segment consisting of two adjacent vertebral bodies, the intervertebral disc, associated ligaments, and facet joints. See, Posner, I, et al. A biomechanical analysis of the clinical stability of the lumbar and lumbrosacral spine. Spine 7:374-389 (1982).

As previously described, a natural facet joint, such as facet joint 32 (FIG. 3), has a superior facet 30 and an inferior facet 31. In anatomical terms, the superior facet of the joint is formed by the vertebral level below the joint, which can thus be called the "caudad" portion of the facet joint because it is anatomically closer to the tail bone or feet of the person. The inferior facet of the facet joint is formed by the vertebral level above the joint, which can be called the "cephalad" portion of the facet joint because it is anatomically closer to the head of the person. Thus, a device that, in use, replaces the caudad portion of a natural facet joint (i.e., the superior facet 30) can be referred to as a "caudad" device. Likewise, a device that, in use, replaces the cephalad portion of a natural facet joint (i.e., the inferior facet 31) can be referred to a "cephalad" device.

When the processes on one side of a vertebral body 14 are spaced differently from processes on the other side of the same vertebral body, components of the devices on each side would desirably be of differing sizes as well to account for anatomical difference that can occur between patients. Moreover, it can be difficult for a surgeon to determine the precise size and/or shape necessary for an implantable device until the surgical site has actually been prepared for receiving the device. In such case, the surgeon typically can quickly deploy a family of devices possessing differing sizes and/or shapes during the surgery. Thus, embodiments of the spinal devices of the present invention include modular designs that are either or both configurable and adaptable. Additionally, the various embodiments disclosed herein may also be formed into a kit or system of modular tools that can be assembled in situ to create a patient specific tool. As will be appreciated by those of skill in the art, as imaging technology improves, and mechanisms for interpreting the images (e.g., software tools) improve, patient specific designs employing these concepts may be configured or manufactured prior to the surgery. Thus, it is within the scope of the invention to provide for patient specific devices with integrally formed components that are pre-configured. Further, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., Essentials of Radiologic Science, Fosbinder and Kelsey, 2002, The McGraw-Hill Companies, publisher; X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher.

A configurable modular device design, such as the one enabled by this invention, allows for individual components to be selected from a range of different sizes and utilized within a modular device. One example of size is to provide caudad and cephalad stems of various lengths. A modular implantable device design allows for individual components to be selected for different functional characteristics as well. One example of function is to provide stems having different surface features and/or textures to provide anti-rotation capability. Other examples of the configurability of modular implantable device of the present invention as described in greater detail below.

Implantable devices can be configurable such that the resulting implantable spinal device is selected and positioned to conform to a specific anatomy or desired surgical outcome. The adaptable aspect of devices provide the surgeon with customization options during the implantation or revision procedure. It is the adaptability of the device systems that also provides adjustment of the components during the implantation procedure to ensure optimal conformity to the desired anatomical orientation or surgical outcome. An adaptable modular device allows for the adjustment of various component-to-component relationships. One example of a component-to-component relationship is the rotational angular relationship between a crossbar mount and a crossbar in an implantable device. Configurability may be thought of as the selection of a particular size of component that together with other component size selections results in a custom fit implantable device. Adaptability then can refer to the implantation and adjustment of the individual components within a range of positions in such a way as to fine tune the "custom fit" devices for an individual patient. The net result is that embodiments of the modular, configurable, adaptable spinal device and systems of the present invention allow the surgeon to alter the size, orientation, and relationship between the various components of the device to fit the particular needs of a patient during the actual surgical procedure. Tools that are configurable and adaptable in a manner similar to the devices are contemplated by the invention to achieve optimal device selection for a patent.

Figure 5:
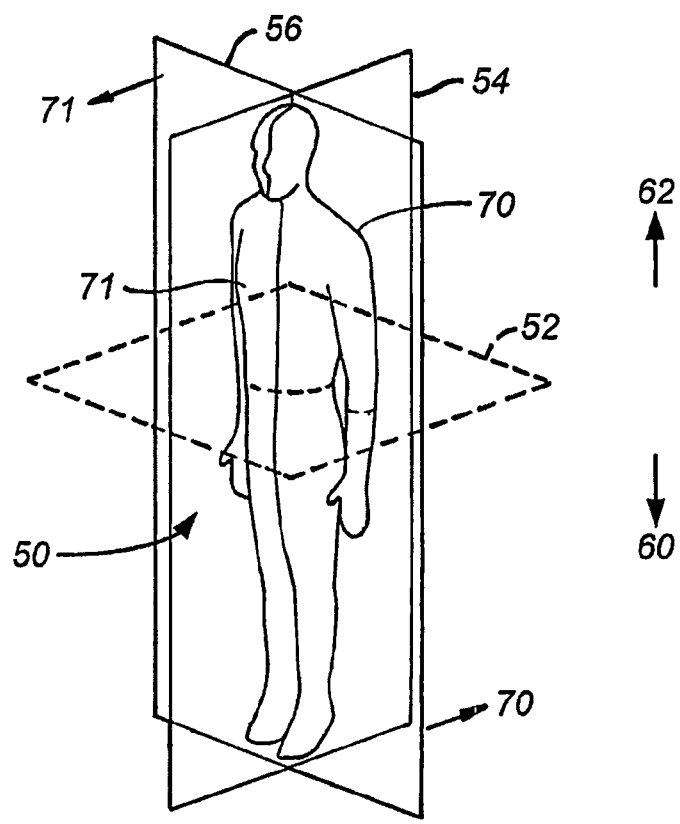
FIG. 5 is a perspective view of the anatomical planes of the human body.

In order to understand the configurability, adaptability, and operational aspects of the invention, it is helpful to understand the anatomical references of the body 50 with respect to which the position and operation of the devices, and components thereof, are described. There are three anatomical planes generally used in anatomy to describe the human body and structure within the human body: the axial plane 52, the sagittal plane 54 and the coronal plane 56 (see FIG. 5). Additionally, devices, tools, and the operation of devices and tools are better understood with respect to the caudad 60 direction and/or the cephalad direction 62. Devices positioned within the body can be positioned dorsally 70 (or posteriorly) such that the placement or operation of the tools or device is toward the back or rear of the body. Alternatively, devices can be positioned ventrally 72 (or anteriorly) such that the placement or operation of the tool or device is toward the front of the body. Various embodiments of the spinal devices, tools and systems of the present invention may be configurable and variable with respect to a single anatomical plane or with respect to two or more anatomical planes. For example, a component or tool may be described as lying within and/or having adaptability or operability in relation to a single plane. For example, a stem may be positioned in a desired location relative to an axial plane and may be moveable between a number of adaptable positions or within a range of positions. Similarly, the various components can incorporate differing sizes and/or shapes in order to accommodate differing patient sizes and/or anticipated loads.

Figure 6:
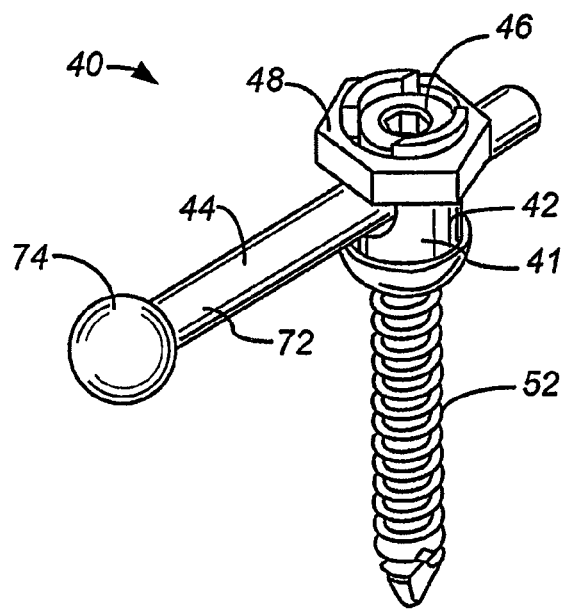
FIG. 6 is a perspective view of a cephalad facet joint implantable device suitable for replacing the inferior half of a natural facet joint on a superior vertebral body.

For purposes of illustrating the invention, an example of a cephalad facet joint that is suitable for use with the measurement tools and methods described herein is depicted in FIG. 6. See also, US 2005/0131406 A1 (Reiley, et al.) FIG. 6 shows an artificial cephalad facet joint 40 configured to replace the inferior articulating process of a facet joint 31, such as after the surgical removal of the articulating process. When the cephalad facet joint 40 is attached to a vertebra, the artificial facet joint element 44 articulates with the superior half of the facet joint 32. In this example, artificial facet joint 40 includes an artificial facet joint element 44 connected to a fixation element 52 via a polyaxial connection 41 that permits facet joint element 44 and fixation element 52 to be rotated with respect to each other around more than one axis. A fixing nut 48 is threadably engaged with the outer periphery of base 42 above the artificial facet joint element 44. Similarly, a set screw 46 is threadably engaged with the inner periphery of base 42 above the artificial facet joint element 44. The artificial facet joint element 44 includes a support arm 72 and a facet joint bearing surface 74. In alternative embodiments, other convex or concave shapes may be used for the facet joint bearing surface 74. Bearing surface 74 may be formed from biocompatible metals (such as cobalt chromium steel, surgical steels, titanium, titanium alloys, tantalum alloys, aluminum, etc.), ceramics, polyethylene, biocompatible polymers, and other materials known in the orthopedic arts. Fixation element 52 may be a screw, stem, corkscrew, wire, staple, adhesive, bone, and other materials known in the orthopedic arts.

Figure 7A:
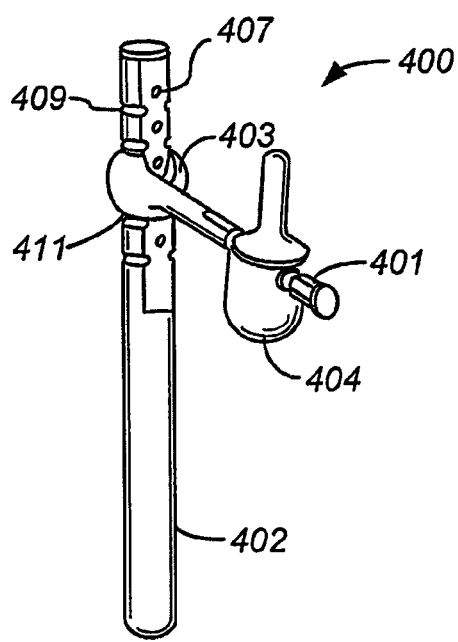
FIG. 7A-B are views of one embodiment of a measurement tool for installing a cephalad facet joint.
Figure 7B:
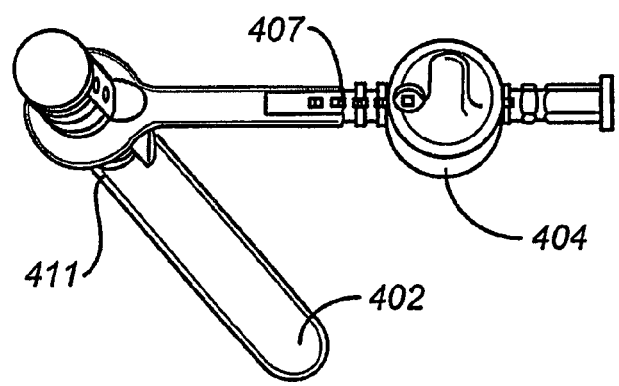

As shown in FIGS. 7A and 7B, a measurement tool 400 suitable for use in installing and configuring the artificial facet joint 40 of FIG. 6 includes a support arm element 401 and a fixation measurement element 402 via a polyaxial connection element 403. The polyaxial connection element 403 permits movement of the support arm element 401 along the fixation measurement element 402 in multiple axes. The connection 403 permits vertical movement of the support arm element 401 along the fixation measurement element 402 (or fixation element) and also permits horizontal movement of the support arm element 401 relative to the fixation measurement element 402. In this manner, the measurement tool contains aspects of the actual artificial facet joint 40. Measurement tools optimized to aid in the implantation of other implantable spinal devices may have other features containing aspects of those devices.

The fixation measurement element 402 is adapted and configured to permit measurement of the length of a fixation element of an artificial cephalad facet joint to be installed in a patient. Preferably, markings 407 are present on the fixation measurement element 402 which permit the determination of this length measurement. Typically, a hole or cavity is formed in the vertebra of the patient at a location wherein the artificial cephalad facet joint 40 is intended to be installed and the measurement tool 400 is placed in this hole. The tool 400 is adjusted to a position similar to that of the artificial cephalad facet joint, and then the penetration depth of the fixation measurement element 402 into the hole is determined. This penetration depth assists the user in choosing the length of the fixation element required to attach the artificial cephalad facet joint to the vertebra.

In one embodiment, the fixation measurement element 402 includes indentations 411 such as those depicted in FIG. 7A. The indentations 409 provide stops for the vertical movement of the support arm 401 along the fixation measurement element 402, e.g., by engaging a ridge 411 in a support arm 401. The indentations 409 can also permit the determination of the length of the fixation element 52 of an artificial cephalad facet joint 40 to be installed in a patient. The indentations 409 may be formed at intervals corresponding to various fixation stems or screw lengths contained in a modular component kit.

Similarly, another length measurement can be obtained using the support arm element 401. Once the measurement tool 400 is placed into the hole or cavity drilled in the vertebra, the support arm 401 is positioned into a location wherein the artificial facet joint element 44 of the artificial cephalad facet joint 40 would be located. The distance between the fixation measurement element 402 and the putative location of facet joint bearing surface 74 of the artificial cephalad facet joint 40 is measured along the support arm element 401. This measurement is used to select the length of the support arm 72 of the cephalad facet joint 40 to be implanted in a patient. Alternatively, the measurement could correspond to a color coding or number/letter designation that is used to determine the appropriate correspondingly-identified artificial facet joint.

In one embodiment, a trial facet joint bearing surface 404 can be attached to the support arm element 401. The trial facet joint bearing surface 404 may be placed in the location that the actual artificial cephalad facet joint 40 would be placed and then the length measurement can be obtained which can be used to select the length of the support arm 72 of the artificial cephalad facet joint 40. Once again, the relationship between the measurement tool's fixation measurement element, support arm element and trial facet joint bearing surface corresponds to aspects of the actual facet joint whose implant the tool is assisting. Other measurement tools and methods having aspects corresponding to other spine implant features are within the scope of this invention.

Figure 8A:
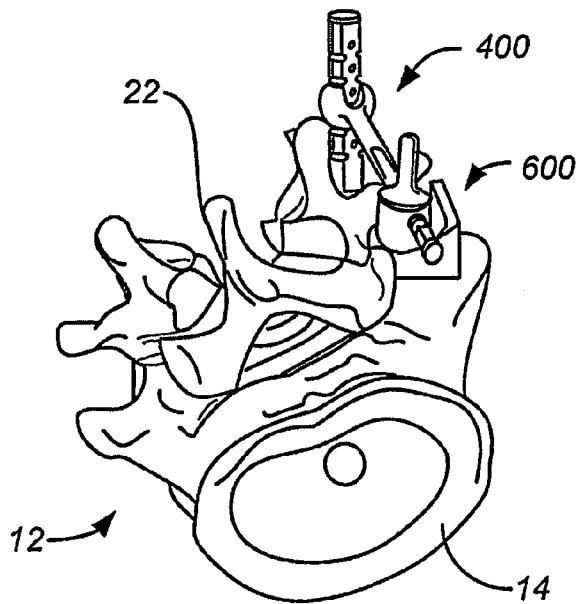
FIGS. 8A, 8B and 8C are views of one embodiment of an installed measurement tool for an artificial cephalad facet joint.
Figure 8B:
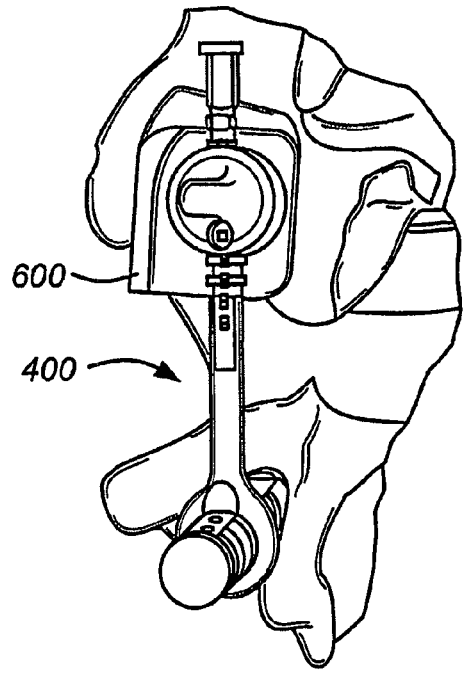
Figure 8C:
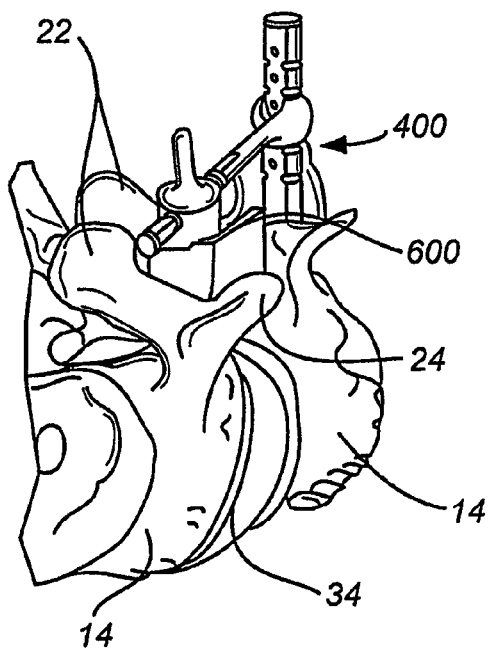

Another aspect of the invention is a method of using the measurement tool 400 to measure the dimensions of an artificial cephalad facet joint 40 to be used in total facet joint replacement. The artificial cephalad facet joint 40 is typically attached to a vertebra to replace the articulating function of the cephalad portion of the natural facet joint 32. FIG. 8 shows different views of a measurement tool 400 placed into a vertebra 12. In one embodiment, for obtaining the measurements, the cephalad measurement tool 400 can be placed in one vertebra and a caudad facet joint 600 can be placed in the inferior adjoining vertebra, as depicted in FIG. 8A. The artificial caudad facet joint can be a trial device or the actual artificial facet joint. When the measurement tool 400 is used with an artificial caudad facet joint, it is preferred that the support arm element 401 have a trial facet joint bearing surface 404. To obtain the length measurements, a hole is formed in the location on the spine where the actual artificial cephalad facet joint 40 (not shown) is to be placed. The tool 400 is placed in the hole formed in the spine at a depth that is similar to the depth at which actual artificial cephalad facet joint 40 is to be placed. The support arm 401 is moved horizontally and/or vertically with respect to the fixation measurement element 402 and placed at about the same location that the artificial facet joint element 44 would be placed. If the measurement tool 400 includes a trial cephalad facet joint bearing surface 404 and is used in combination with an artificial caudad facet joint 600, the trial facet joint bearing surface 404 is placed in the bearing surface of the caudad facet joint prior to taking the measurements. In one embodiment, as shown in FIGS. 7B and 8B, to determine the length of the support arm 72 of the actual artificial cephalad facet, a window on the trial facet joint bearing surface 404 can be used to read the length from the support arm element 401. As mentioned above, the length of the fixation element 52 can be determined from the fixation measurement element 402. Markings 407 and/or indentations 409 on the fixation measurement element 402 can be used to determine the required length of the fixation element 52. Markings 407 are positioned to correspond with indentations on the fixation measurement element 402 such that when the polyaxial connection element 403 is engaged with the measurement element 402, e.g., by engaging the indentation 405 in the fixation measurement element 402 with a ridge 402 a protrusion on the polyaxial connection element 403, a measurement is ascertainable by the user.

FIG. 9 shows an artificial caudad facet joint 100 configured to replace the superior portion of a natural facet joint 30, such as after the surgical removal of the articulating process forming the superior portion of the facet joint. Artificial caudad facet 100 includes an artificial facet joint element 104 connected to a fixation element 116 via a polyaxial connection 115 that permits facet joint element 104 and fixation element 116 to be rotated with respect to each other around more than one axis. The polyaxial connection 115 of artificial caudad facet joint 100 includes a base 112 connected to a support arm 102 of facet joint element 104. The artificial facet joint element 104 includes a bearing surface 118. A fixing nut 108 is threadably engaged with the outer periphery of base 112 above the artificial facet joint element 104. Similarly, a set screw 106 is threadably engaged with the inner periphery of base 112 above the artificial facet joint element 104.

FIGS. 10-12 depict one embodiment of a measurement tool for installing an artificial caudad facet joint 100. The measurement tool can be used to assist in the installation of artificial caudad facet joint such as those described in U.S. Patent Pub. US 2005/0131406 A1 (Reiley, et al.) or other caudad facet joint.

A measurement tool 700 suitable for use with the artificial caudad facet joint shown in FIG. 9 is shown in FIGS. 10A and 10B. Measurement tool 700 includes a stem element 701 connected to a trial caudad bearing surface 702 via a fastener 703. Thus, measurement tool 700 contains aspects of the artificial caudad facet joint 100 whose implant the tool is assisting. In the embodiment depicted in FIG. 10A, the fastener 703 is a set screw. In other embodiments other suitable fasteners can be employed, including, but not limited to, sterns, posts, threads, polyaxial mechanisms, splines, cap screws, ball detents, friction fits, tapers, press fits, bayonet, cams, collets and/or clamps.

The stem element 701 is adapted and configured to obtain length measurements which would correspond to the length of the fixation element 116 of the artificial caudad facet joint 100. The stem element 701 can include markings and/or indentations such as those depicted with respect to the cephalad tool 400 shown in FIG. 8 to assist in obtaining the measurements. If desired, multiple stem elements of varying diameters and lengths can be utilized in a similar fashion to size and/or determine the diameter and dimensions of the hole or cavity.

The trial caudad bearing surface 702 helps determine the relative positions of, and the angle between, the artificial facet joint's fixation element and its bearing surface. The trial caudad bearing surface 702 is capable of movement along multiple planes and can rotate relative to the stem element 701 via a lockable ball joint or other suitable joint configuration. If desired, an alternate embodiment of the bearing surface 702 can move vertically (not shown) along the stem element 701, to permit sizing of the stem element 701. Other planes of movement can include the median, horizontal and frontal planes as well as the sagittal, coronal, and axial shown in FIG. 5. In another embodiment, the caudad bearing surface 702 is connected to a handle 704. The handle 704 allows the user to move the caudad bearing surface 702 into the desired location and also position it in the right plane. Typically, the handle 704 permits movement of the caudad bearing surface 702 in various planes for alignment. Also, the handle 704 can permit the user to place the stem 701 of the tool 700 into the hole drilled in the vertebra.

In one alternate embodiment, the handle 704 can comprise a radiopaque material with the handle 704 used for fluoroscopic alignment of the caudad bearing surface 702. By using radiopaque materials that do not allow the passage of x-rays or other radiation through the part, a physician can see the instrument when radiologic imaging techniques are used. In this embodiment, the handle 704 and upper end plate of the caudad vertebral body (not shown) can be examined in a medial-lateral image (using non-invasive and/or fluoroscopic imagine apparatus) of the surgical area. A comparison of the orientation of the handle 704 and the orientation of the upper end plate can be made to determine the desired alignment and positioning of the caudad bearing surface. In one embodiment, the orientation of the handle and the upper end plate can be parallel or nearly parallel.

Figure 11A:
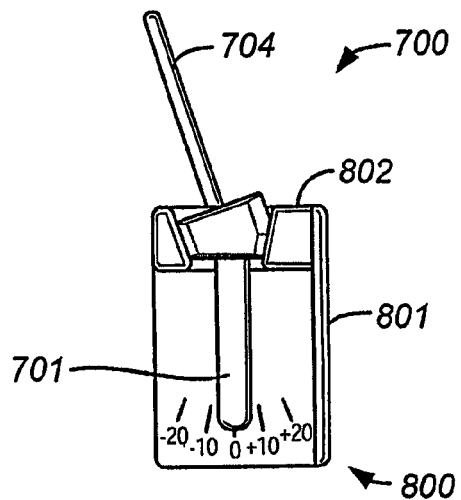
FIGS. 11A-D are views of one embodiment of a measurement tool holder for holding a measurement tool for a caudad cephalad facet joint.
Figure 11B:
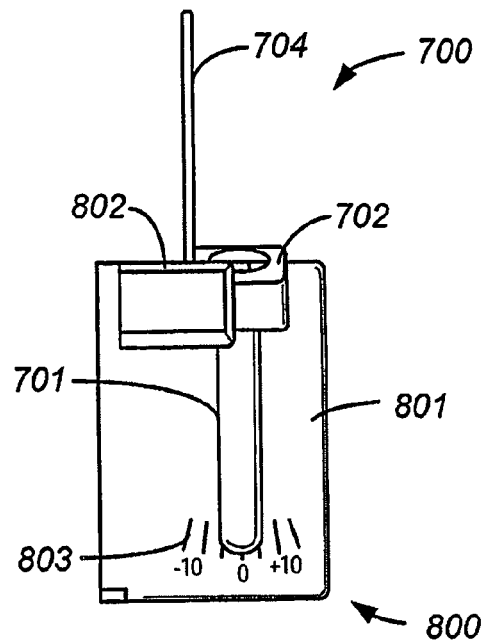
Figure 11C:
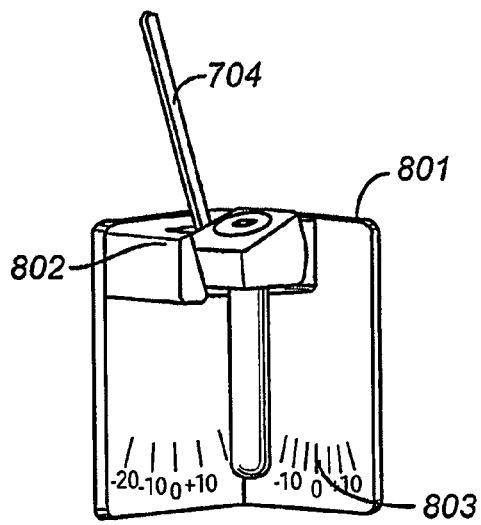
Figure 11D:
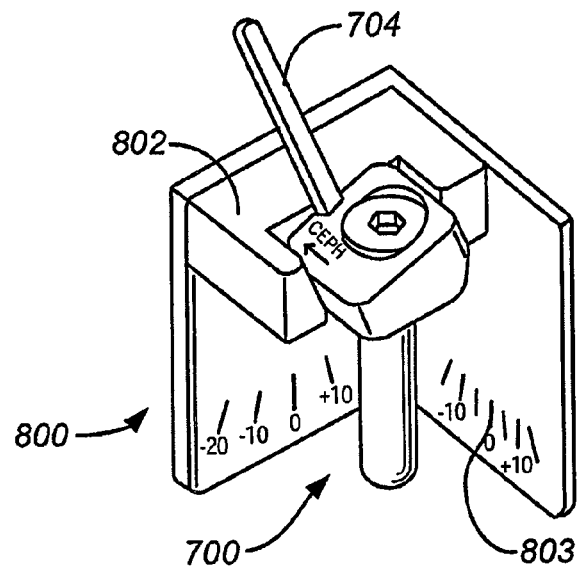

Another aspect of the invention is a measurement tool holder for use with the caudad measurement tool 700 described above or another measurement tool. One embodiment of the measurement tool holder is depicted in FIGS. 11A-D. In this embodiment, the measurement tool holder 800 includes a measurement surface 801 and a holder element 802. In one embodiment, the measurement surface 801 includes two plates attached to each other at a right angle, as illustrated in FIG. 11C-D. The measurement surface 801 is adapted and configured to measure the angle between the caudad bearing surface 702 and stem 701. This angle measurement is typically used by a user to select, assemble and/or configure an artificial caudad facet joint 100 for implantation into a patient, such as artificial caudad facet joint 100 of FIG. 9. For example, the selected artificial caudad facet joint 100 may have an angle measurement between its bearing surface 118 and its fixation element 116 similar to the angle measurement obtained from the caudad measurement tool 700 and measurement tool holder 800. Alternatively, the artificial caudad facet joint may be configurable to orient its fixation element 116 and its bearing surface 118 to match the measured angle.

In one embodiment, the tool holder's 800 measurement surface 801 includes markings 803 to assist in obtaining the desired angle measurements. Also, the top surface of the measurement surface 801 may have a holder element 802 attached thereto. The holder element 802 can be, for example, a square or rectangular block with a portion of the block cut-out to fit the caudad bearing surface 702 of the caudad measurement tool 700. Alternatively, the block can be configured to engage the measurement tool 700 the portion of the holder element 802 that holds the caudad bearing surface 702 is cut-out in a shape that is suitable for holding the caudad bearing surface 702. Thus, the shape of the cut-out portion of the holder element 802 will vary depending on the shape of the caudad bearing surface 702 to be used with the measurement holder 800.

Figure 12A:
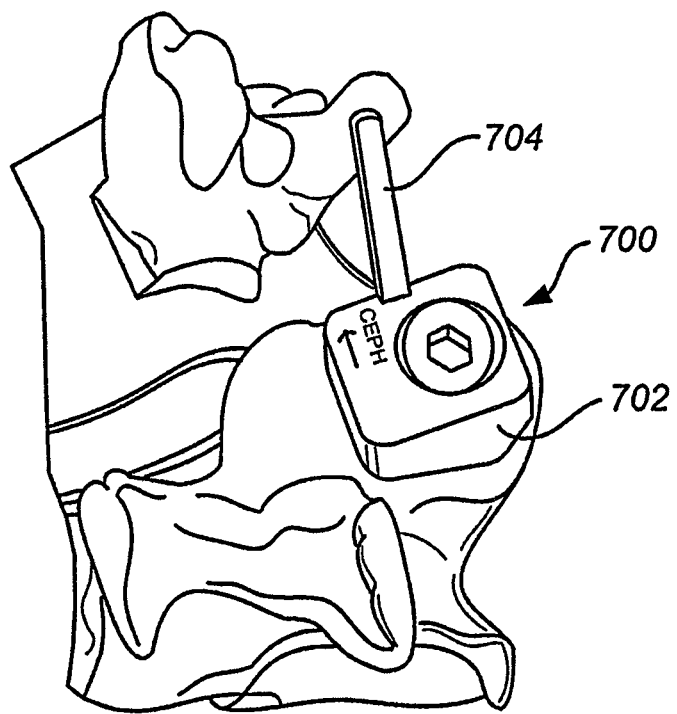
FIGS. 12A and 12B are views of one embodiment of an installed measurement tool for a caudad cephalad facet joint.
Figure 12B:
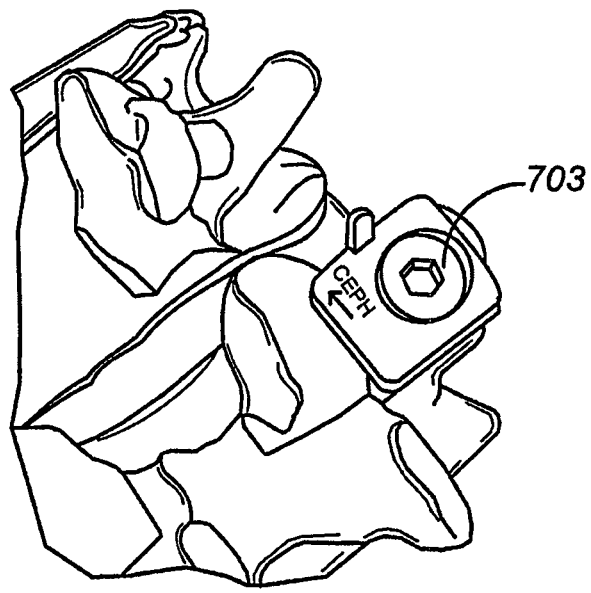

One aspect of the invention is a method for using the caudad measurement tool 700 in combination with, for example, the measurement tool holder 800 described above or with the cephalad measurement tool 400 described above. In one embodiment, a hole is formed at a suitable location in the vertebra (such as by drilling) wherein an artificial caudad facet joint 100 is intended to be placed. This location typically is the best location for the placement of the artificial caudad facet joint based on the condition of the bone, easy access to the location, etc. Into this hole the caudad measurement tool 700 is placed in a manner as shown in FIGS. 12A and 12B.

The caudad measurement tool 700 may be placed into the hole using the handle 704. The handle 704 and the set screw 703 are used to place the measurement tool at the required depth and also to place the caudad bearing surface 702 at the required angle. To obtain the appropriate angle of the caudad bearing surface 702 with respect to the stem 701, the fastener 703 is loosened and the caudad bearing surface 702 is positioned at the appropriate angle. Once the appropriate angle is obtained (typically based on orientation relationships with anatomical landmarks, which can include the orientation of the cephalad bearing surface as well as anatomical positioning and/or intervening anatomical features), the fastener 703 is tightened to maintain the angle for measurement purposes. In one embodiment, the caudad measurement tool 700 is used in combination with an artificial cephalad facet joint (such as artificial cephalad facet joint 40 described above) or a cephalad measurement tool (such as tool 400 described above). When used in combination with an artificial cephalad facet joint or a cephalad measurement tool, the caudad bearing surface 702 is placed in contact with the facet joint bearing surface of the artificial cephalad facet joint or the trial facet joint bearing surface. Then, the position of the caudad bearing surface 702 is adjusted by manipulating the fastener 703 (as described above) to get good articulation with the facet joint bearing surface or the trial facet joint bearing surface.

After the caudad measurement tool 700 is appropriately placed, the length and angle measurements are obtained. Preferably, the caudad measurement tool 700 is removed from the hole to take the measurements. One of the measurements that can be obtained with the caudad measurement tool 700 is the fixation length measurement. This measurement is obtained from the stem element 701 and indicates the length of the fixation element 116 of the artificial caudad facet joint to be implanted in a patient. Also, the caudad measurement tool 700 can be used to obtain an angle measurement between the caudad bearing surface 702 (or alignment fixation measurement) and stem element 701. This measurement may be obtained by placing the caudad measurement tool 700 into a measurement tool holder (such as holder 800 described above) and reading the angle, such as from a measuring surface 801. When used with the artificial caudad facet joint 100 of FIG. 9, this angle measurement is used to determine the angle between the artificial facet joint element 104 and fixation element 116 of the artificial caudad 100. In one alternate embodiment, the caudad bearing surface is positioned and secured to the vertebral body first, and then the cephalad bearing surface is positioned and secured relative to the caudad bearing surface.

One aspect of the invention is a method for selecting suitable caudad and/or cephalad artificial joints from a set of artificial joints for implantation into a patient. In one embodiment, the cephalad measurement tool 400 is used to obtain the two length measurements from the fixation measurement 402 and support arm 401. A user uses these measurements to select a suitable artificial cephalad facet joint 40 for implantation in a patient. The selected artificial facet joint preferably has a fixation element 52 length and support arm 72 length that are similar to the support arm 401 and fixation measurement 402 length measurements, respectively, obtained from the cephalad measurement tool 400. As will be appreciated, similar includes lengths that have values that correspond to each other but are not necessarily identical. In another embodiment, the caudad measurement tool 700 is used to obtain length and angle measurements and a user uses these measurements to select a suitable artificial cephalad facet joint for implantation in a patient. The selected artificial facet joint preferably has a stem 701 length similar to the length measurement from the caudad tool 700 and has an angle between the artificial facet joint element and fixation element similar to the angle measurement obtained from the tool.

Figure 13A:
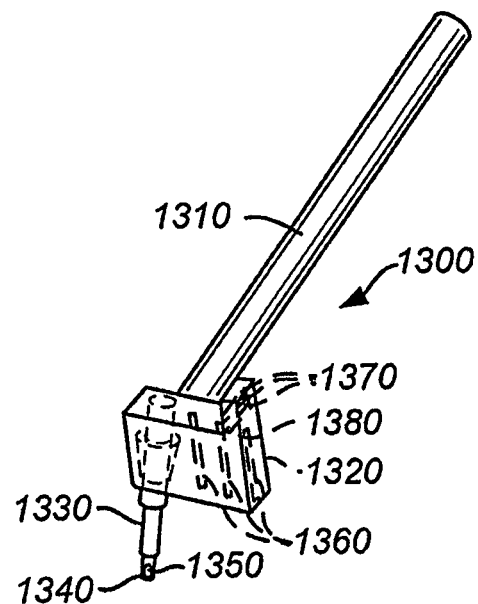
FIGS. 13A-B are views of another embodiment of a measurement tool for a caudad facet joint.
Figure 13B:
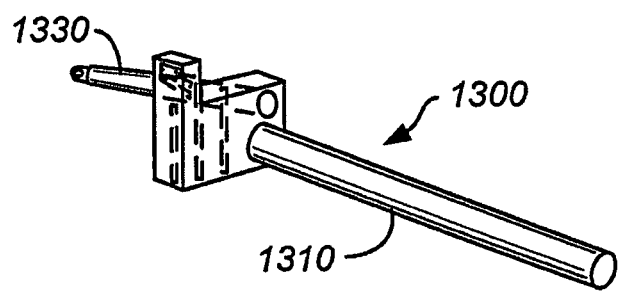

Yet another alternate device and method for determining the proper size and orientation of the artificial facet joint is illustrated in FIGS. 13A-B. A tool such as a component selection instrument 1300 is illustrated that is useful for determining the proper combination of caudad anchor stem, as well as the caudad cup best suited for a targeted anatomy. In this embodiment, a component selection instrument 1300 comprises a handle 1310, a body 1320 and a stem 1330, each of these preferably comprising a radiolucent material. Within the body 1320 and the distal tip 1340 of the stem, radiopaque markers 1350, 1360 and 1370 are positioned, such that, when the stem 1340 is inserted into a pilot hole (not shown) of a targeted vertebral body in a spine, upon radiographic visualization of the vertebral body, the radiopaque markers align to indicate the proper combination of components for the targeted region, while the radiolucent instrument allows the physician to view the markers relative to the patient's anatomy.

Specifically, the depicted embodiment of a component selection instrument 1300 incorporates a distal radiopaque marker 1350 positioned within the distal tip 1340 of the stem 1330. A series of stem selection radiopaque markers 1360 (in this embodiment, three markers) are positioned within the housing. As will be appreciated by those skilled in the art, more or fewer markers can be used. A series of cup selection radiopaque markers 1370 (in this embodiment, three markers) are also positioned within the housing. If desired, the component selection instrument 1300 can be optimized for single-sided use (for measurement of only the left or right pedicle) or for dual-sided use (for example, the component selection instrument could be adapted and configured to incorporate symmetrical radiopaque markers that provide the proper measurements depending upon the orientation of the instrument. Additionally, as discussed more fully below, the markers can be given exterior dimensions that present different profiles during radiography in order to facilitate an ease in determining which set of markers is being viewed.

Once the stem 1330 is inserted into the pilot hole or cavity (not shown), the interior edge 1380 of the housing 1320 (the edge nearest the centerline or midline of the spine in the body (see FIG. 5)) is visually aligned with the spinous process 22 of the vertebral body (see FIGS. 1-4). Once the visual alignment is achieved, radiologic techniques known in the art can be used to obtain a view of the target anatomy along with the component selection instrument, such as an anterior/posterior (A/P) view of the spine and component selection instrument 1300 using a fluoroscope. Depending upon the lateral angle of the pedicle, the distal radiopaque marker 1350 will line-up with (or will appear closest to) one of the stem selection radiopaque markers 1360, each of which correspond to a different stem angle. After taking the A/P view, the physician can then take a lateral view of the spine and component selection instrument 1300. From the lateral view, the physician can then align the cephalad endplate of the caudad vertebral body (not shown) with the most appropriate cup selection radiopaque marker, which gives the proper cup size for implantation. (See, FIG. 23). Alternatively, a lateral view can be taken first, or only one of the A/P or lateral view can be taken and analyzed.

The caudad stem may be secured directly into the vertebral body, or can be attached and/or "fixed" using a supplemental fixation material such as bone cement, allograft tissue, autograft tissue, adhesives, osteo-conductive materials, osteo-inductive materials and/or bone scaffolding materials. In one embodiment, the first fixation element can be enhanced with a bony in-growth surface, such as surfaces created using sintering processes or chemical etching (Tecomet Corporation of Woburn, Mass.) which can help fix the fixation element within a vertebra. As described above, the bony in-growth surface can cover all or a portion of the caudad fixation element. Desirably, the final orientation of the caudad cups of the caudad facet joint 600 (FIGS. 8B and 9) will be parallel (relative to the lateral walls 159 of the caudad cup) and coplanar (with respect to the upper bottom surfaces 153).

Figure 14A:
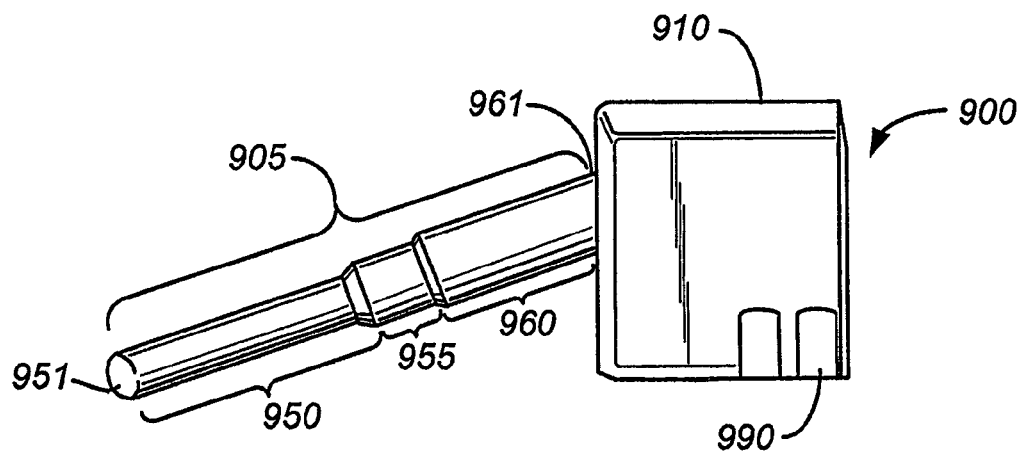
FIGS. 14A-C are views of a measurement tool for a caudad facet joint.
Figure 14B:
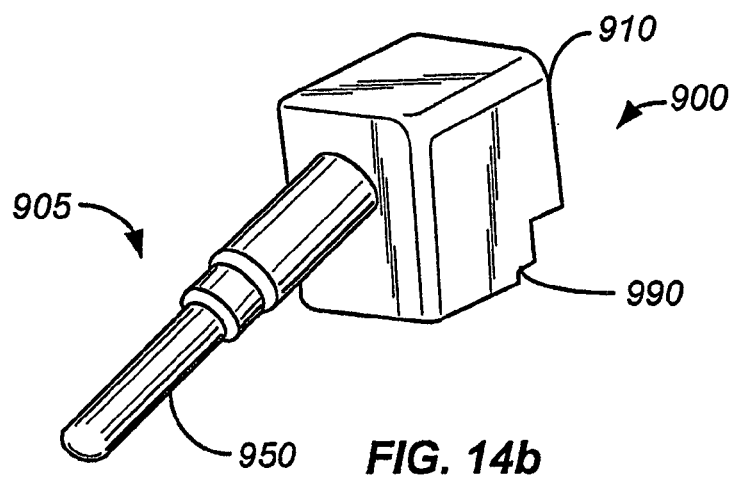
Figure 14C:
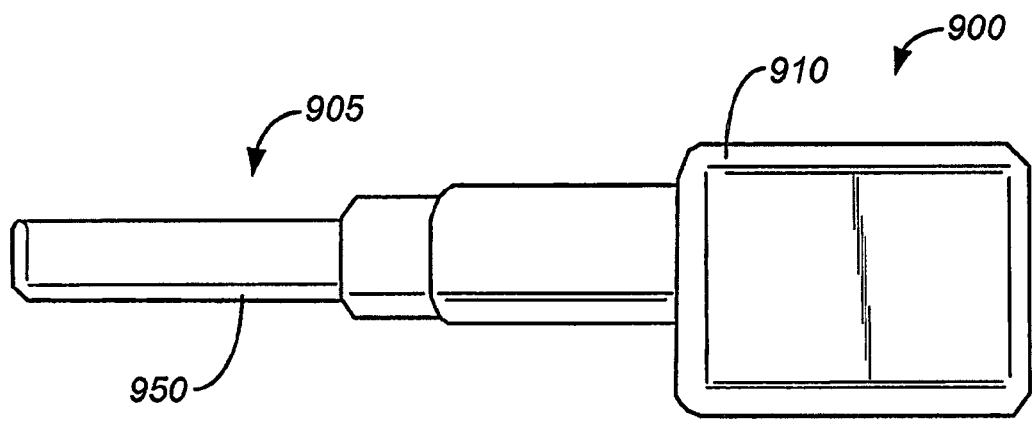

FIG. 14A depicts a top plan view of an alternate embodiment of a component selection instrument 900 constructed in accordance with various teachings of the present invention. The component selection instrument 900 comprises a stem 905 and a head 910, both of which, in this embodiment, are desirably (but not necessarily) constructed of radiolucent materials (or alternative materials useful in conjunction with the present invention, including those that desirably facilitate the use of non-direct visualization such as fluoroscopy, real-time CT scanning and/or real-time MRI). The stem comprises a distal section 950 (distal from the block) having a distal end 951, a central section 955, and a proximal section 960. The stem 905 is configured to engage the head 910 at its proximal end 961. The stem 950 can be positioned such that it extends from the head 910 at an angle other than 90° in at least one direction. Thus, as evident from FIG. 14A, a side view of the component selection instrument 900, the head 910 is positioned on a first geometric plane, while the stem 905 extends from the head 910 such that the stem 905 crosses, or could cross if the stem had sufficient length, the geometric plane on which the head 910 is positioned. In contrast, as illustrated in FIG. 14c, a view of the instrument 900 taken from a top view, the stem 905 extends from the head 910 such that it appears from this two-dimensional perspective that the stem 905 and the head 910 lie within the same plane. FIG. 14B illustrates a perspective view of the instrument 900. The head 910 can be configured with an indentation, slot or keyway 990 which is adapted to engage a tool, such as the tool shown in FIG. 17.

Figure 15A:
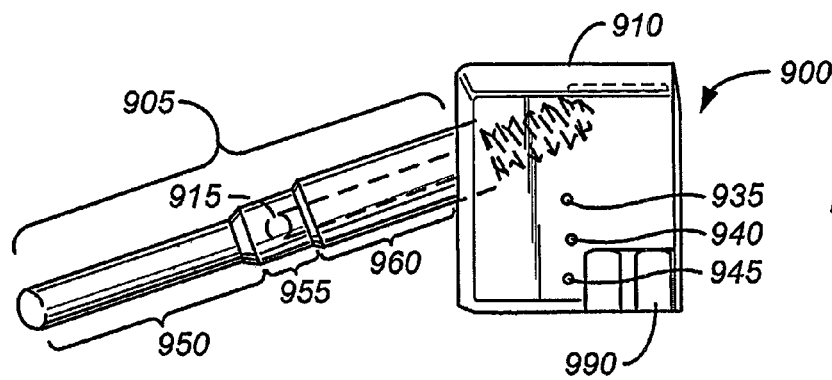
FIGS. 15A-D are views of a measurement tool illustrating the interior component of a measurement tool for a caudad facet joint.

As illustrated in FIG. 15A, which depicts the same component selection instrument 900 enabling the internal portion of the instrument to be viewed, one or more radiopaque markers are contained within the stem 905 and head 910. These markers are desirably positioned such that, when the component selection instrument 900 is secured to the targeted vertebral body, one or more non-direct visualization methods can be used to compare the visible anatomical landmarks to the various markers incorporated in the component selection instrument (as well as the various inter-relationships between markers and/or the anatomical features themselves) to determine the anatomical characteristics of the components of the targeted vertebral body, as well as the relationship therebetween. This invention allows the physician employ minimally invasive techniques to select the optimal implantable artificial joint components to accommodate the targeted patient anatomy. In addition, the unique orientation and positioning of the radiopaque markers within the stem 905 and head 910 can obviate the need for an "adjustable," or articulating, facet measurement devices, thereby significantly simplifying the construction and/or use of the device.

Thus, turning to FIG. 15, the component selection instrument 900 incorporates a radiopaque marker 915 positioned within the stem 905. The radiopaque marker 915 can be in a variety of suitable configurations, such as a ball, as depicted which would present a circular image in a two dimensional image, such as an x-ray. The radiopaque ball 915 and various marker elements in the head 910 are arranged to allow determination of the orientation of the stem 905 relative to a given anatomical feature and/or arbitrary reference plane. In addition, a first marker 920 can be positioned within the head 910. As will be described later, this first marker 920 can be used to determine the angle of the stem 905 relative to a cephalad endplate (not shown) of the vertebral body in which the component selection instrument is placed. One or more second markers 935, 940 and 945 (which may be parallel to each other and/or within the same plane) can also be positioned within the head 910, and are desirably used, in conjunction with the ball 905. As will be appreciated by those skilled in the art, either or both sets of first and second markers can be used without departing from the scope of the invention. Further, the first set of markers can be in a first orientation, e.g. horizontal, while the second set of markers can be in a second orientation that is different than that of the first set of markers, e.g. vertical, where horizontal and vertical can be in relation to a defined plane in the body or an arbitrary plane used to describe the location of one set of markers with respect to the second set of markers, given that the actual location of the component selection instrument within a human body can change depending upon the location in the spine where the instrument is used. Either or both sets of markers is useful for determining the orientation of the stem 905 in relation to a sagittal plane passing vertically through a targeted vertebral body (see, FIG. 5). As depicted the stem 905 is configured to engage the head 910 by, for example, threadably engaging the proximal end of the stem 905. For this purpose, the proximal end of the stem 905 has a plurality of threads 906 that engage grooves 908 located within the head 910.

In an embodiment, the stem 910 can be configured such that it has a hollow aperture 912 through a portion thereof. The hollow aperture can be used to house the distal end 950 of the stem 910. Thus, providing a telescoping effect for the stem 910 which enables the stem to achieve variable lengths in operation. Where a telescoping stem 910 is used, a first pilot hole can be drilled into the vertebral body of a first diameter. The telescoping stem 910 can then be inserted into the pilot hole a distance corresponding to the length of the distal end 950 of the stem 910 which has a diameter that is sized to engage the first pilot hole. Subsequently, a second pilot hole can be drilled which enlarges or revises the diameter of the first pilot hole and uses the first pilot hole as a basis. Upon obtaining a second pilot hole, the stem 910 can be reinserted into the pilot hole. In one instance, the telescoping distal end 950 can be retracted into the lumen of the proximal end of the stem enabling the larger diametered distal end to be inserted into the pilot hole. Alternatively, the pilot hole can be of sufficient depth to enable it to accommodate the entire length of the stem 910, which the upper region of the pilot hole having a diameter sized to engage the larger diameter of the proximal end of the stem 910. Where the stem 910 is telescoping, the stem could be configured such that when extended, the distal end of the stem is maintained in an extended configuration by, for example, twisting the distal end relative to the proximal end to engage a latch (similar to a child-proof cap configuration). Alternatively, the distal end of the stem could engage one or more detents which engage the distal end in an extended or retracted position. Other solutions would be apparent to those of skill in the art without departing from the scope of the invention.

Figure 15B:
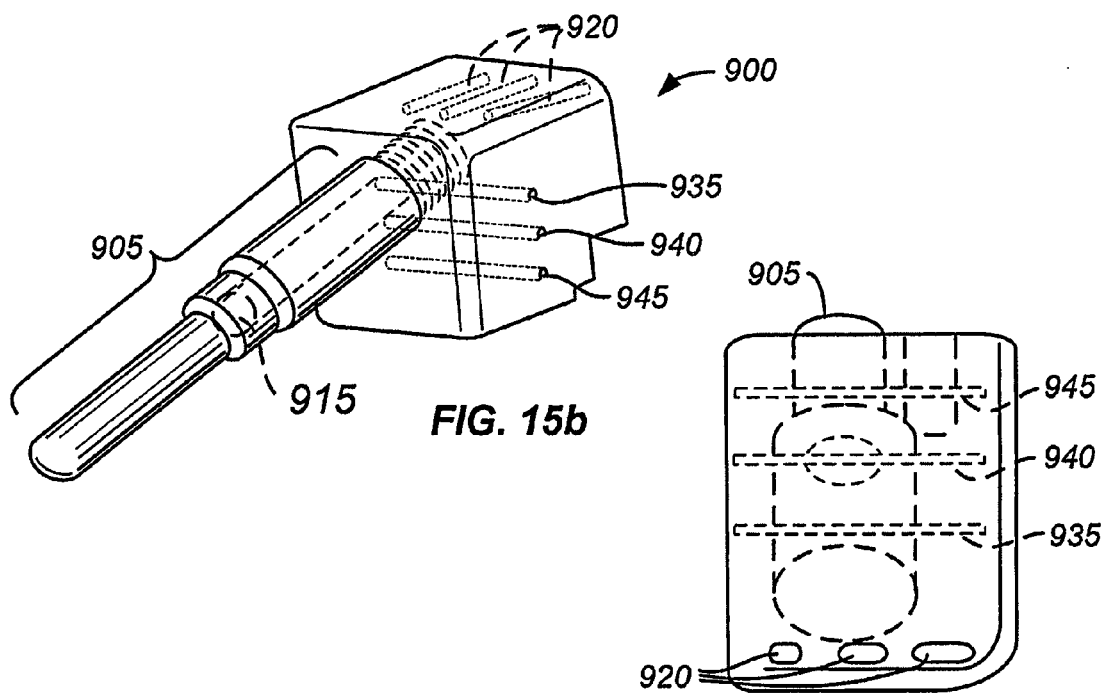

Alternatively, the interior of the stem 910 can be configured from a material that has a radiopacity that is different than the rest of the device (either more radiopaque, or less), thus providing additional visual markers for the physician upon taking an image, such as an x-ray (see, FIG. 15B). The hardness of a first material (e.g. the interior material) can have a hardness, for example a Shore or Rockwell scale value, that is higher or lower than the second (exterior material).

In an exemplary embodiment, a component selection instrument 900 can comprise an approximately 0.8" by 0.5" block of radio-lucent polymer, having an approximately 4.5 cm long stem extending outward from the block. The stem 905 can be configured such that it is stepped by having sections along its lengths of different diameters (see, e.g. FIG. 15). Alternatively, rather than providing changes to the diameter in a step fashion, if desired, the stem 905 can gradually change from a first diameter at a first end to a second diameter at a second end by, for example, use of a slope or slant along the length of the stem.

The polymer or thermoplastic used to make any of the components of the instrument 900, such as the stem 905 or head 910, can comprise virtually any non-radiopaque polymer well known to those skilled in the art including, but not limited to, polyether-etherketone (PEEK), polyphenylsolfone (Radel®), or polyetherimide resin (Ultem®). If desired, the polymer may also comprise a translucent or transparent material, or a combination of materials where a first material has a first radiopacity and the second material has a second radiopacity. Suitable PEEK can include an unfilled PEEK approved for medical implantation such as that available from Victrex of Lancashire, Great Britain. (information on Victrex is located at www.matweb.com or see Boedeker www.boedeker.com). The instruments and tools can be formed by extrusion, injection, compression molding and/or machining techniques, as would be appreciated by those skilled in the art. Other polymers that may be suitable for use in some embodiments, for example other grades of PEEK, such as 30% glass-filled or 30% carbon filled, provided such materials are cleared for use in implantable devices by the FDA, or other regulatory body. The use of glass filled PEEK would be desirable where there was a need to reduce the expansion rate and increase the flexural modulus of PEEK for the instrument. Glass-filled PEEK is known to be ideal for improved strength, stiffness, or stability while carbon filled PEEK is known to enhance the compressive strength and stiffness of PEEK and lower its expansion rate. Still other suitable biocompatible thermoplastic or thermoplastic polycondensate materials mabe be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further other polyketones can be used as well as other thermoplastics. Reference to appropriate polymers that can be used in the tools or tool components can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used as well for portions of the instrument that are desired to be radiolucent.

In the embodiment illustrated, the stem 905 comprises a 2.25 cm long distal section having a 4.5 mm diameter, which transitions to a 0.75 cm long central section having a 5.75 mm diameter, and then transitions to a 2.0 cm long proximal section having a 6.5 mm diameter. Other configurations are possible, including configurations having other lengths, diameters, as well as fewer or more stepped sections.

Figure 15C:
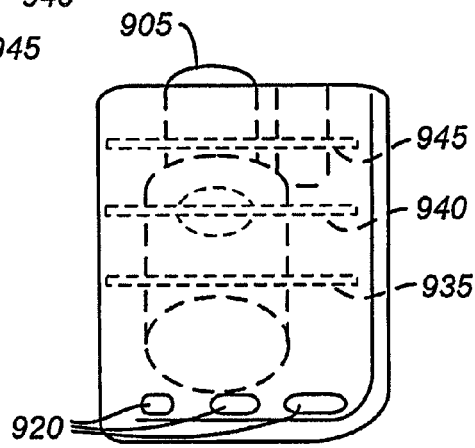
Figure 15D:
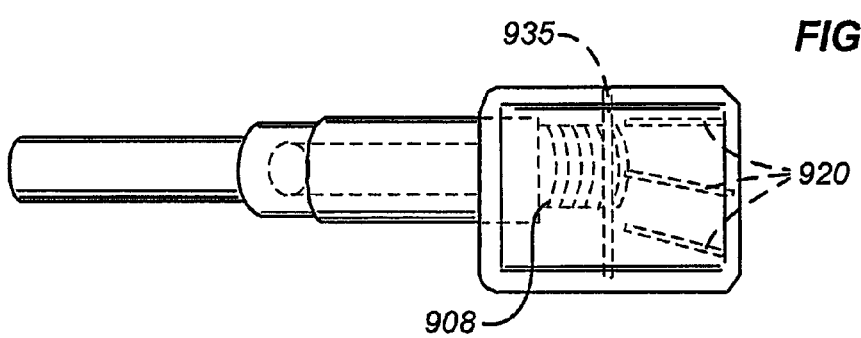

The radiopaque ball 915 (which could comprise, for example, a 2 mm diameter stainless steel ball) is desirably secured inside the central section 955 of the stem. The various first and second set of radiopaque markers 920, 935, 940 and 945 can comprise, for example, 1.5 mm diameter sections of 1 cm long stainless steel wire having a smooth outer surface. As shown in FIG. 15B the component selection instrument can be configured to present a first set of radiopaque markers 920 at a first orientation and a second set of radiopaque markers 935, 940, 945 at a second orientation. As illustrated, the first set of radiopaque markers 920 lie in a first plane and are positioned parallel one another; while the second set of radiopaque markers 935, 940, 945 lie in a second plane that is orientated perpendicular to the first plane. Thus, the position of the first set of radiopaque markers 920 relative to the second set of radiopaque markers 935, 940, 945 is such that in a two-dimensional image, the markers could appear to be perpendicular to each other, as shown in FIG. 5c. This enables the physician to assess the location of the component selection instrument relative to anatomy after radiological imaging. FIG. 15C is a top view of the component selection instrument 900 where the first set of radiopaque markers 920 appear as circles due to the orientation, while the second set of radiopaque markers 935, 940, 945 appear as rods or lengths of wire. In yet another embodiment, illustrated in FIG. 15D the first set of radiopaque markers 920 are configured such that the markers are not parallel one another, while the second set of radiopaque markers are parallel such that in this orientation and from the perspective shown it appears as though there is only one marker although, in fact, more than one marker may be present, but may not be readily apparent because the markers are stacked in two dimensions.

The various stem diameters desirably facilitate and accommodate measurement and verification of proper component sizes during the various stages of facet replacement surgery. For example, in preparation for implantation of a facet replacement device, the surgeon may drill a first pilot hole, e.g. a 4.5 mm passage, into and/or through the pedicle. This small diameter passage, which may be too small to properly accommodate the anchoring device of an artificial facet joint (depending on the diameter and type of anchoring device), is well suited for implantation of a standard commercially-available pedicle screw fusion system (such as the UCR Pedicle Screw System from SeaSpine (information available at http://www.seaspine.com/UCR_Pedicle_Screw_System.html)). Thus, the 4.5 mm distal portion of the stem 910 of the component selection instrument 900 will fit into the 4.5 mm passage drilled into the pedicle, and if the measurement obtained using the component selection instrument indicates that the passage through the vertebral anatomy cannot be accommodated by the components of the artificial facet joint, the surgeon can then choose to (1) redrill or revise the passage and remeasure the passage (e.g., by boring out the original pilot hole with a larger diameter passage and then inserting the component selection instrument into the revised pilot hole), (2) implant the components of the artificial facet joint most closely approximating the anatomy, and/or (3) choose to fuse the targeted spinal level and implant a pedicle screw and rod system. Accordingly, the present measurement system allows the physician to discontinue the facet joint replacement procedure where the anatomy and/or available artificial facet joint components cannot accommodate the targeted spinal level. Alternatively, if the measurement achieved by the component selection instrument indicates that the artificial facet joint can accommodate the patient's specific anatomy, the component selection instrument can be removed, the passage can then be redrilled (if desired) to a larger diameter (in this embodiment, either 5.75 mm or 6.5 mm), and remeasured (if desired) using the larger diameter section of the stem to secure the component selection instrument within the newly drilled passage to ensure proper choice in artificial facet joint components. The artificial facet joint can then be implanted.

FIG. 16 illustrates yet another embodiment wherein the component selection instrument is exploded and markers (e.g., first set of radiopaque markers 920 or second set of radiopaque markers 935, 940, 945) are configured such that the exterior of the radiopaque marker does not present a smooth surface (e.g. markers illustrated previously appear as either a smooth wire or bar (defined by two parallel lines when sitting longitudinally in a first plane as captured by an image) or a circle (representing the diameter of the marker as it appears in a plane 90° offset from the first plane). In this embodiment, employing markers for at least some of the markers that are not configured from, for example, wire having a smooth external surface, the physician would be able to determine which orientation was being looked at in a radiographic image. In this embodiment, a single first marker 920 is employed with three second markers 935, 940, 945 oriented in a plane perpendicular, or substantially perpendicular to the first marker 920. While the alternate configuration of marker could be used, it would also be advantageous to mix the marker profiles within a single component selection instrument such that the markers in a first orientation were, for example, smooth wire, while the markers in a second orientation are turned, e.g. using a lathe with a cutting tool to shape the wire along its length, to create sections with different cross-sectional or circumferential values, etched, or notched. Thus, in an image, the orientation of the component selection instrument relative to the anatomy would be easily determinable based on the appearance of smooth lines or turned, notched or etched surfaces along the length of a marker. In this embodiment, the distal end of the stem is solid while the proximal end of the stem has an aperture 962 that is sized to receive the marker 915 and a tube 964 which fits within the aperture 962 and is sized to retain the marker within the stem 910.

In another embodiment, where two component selection tools 900 are positioned within a vertebral body, or a pair of vertebral bodies, and a single image is taken, the markers 920, 935, 940, 945 can be configured such that the markers in the first component selection tool have a first geometric profile, such as smooth lines, or turned, notched or etched surfaces along the length. While the markers 920, 935, 940, 945 of the second component selection tool have a geometric profile that is not the same as the geometric profile of the markers 920, 935, 940, 945 of the first component selection tool. Thus, for example, markers 920, 935, 940, 945 of the first component selection tool could be smooth wire while markers 920, 935, 940, 945 of the second component selection tool could be turned wire. When using two component selection tools at one time to measure the angle of the desired device, a user could assess by looking at a single image the desired size and configuration of a device for first and second target joint locations by knowing that type of markers in the first component selection tool and its location within the body and the type of markers in the second component selection tool and its location within the body. The component selection instruments could be positioned in a right and left half of a single vertebral body, or could be positioned within adjacent vertebral bodies.

Figure 17A:
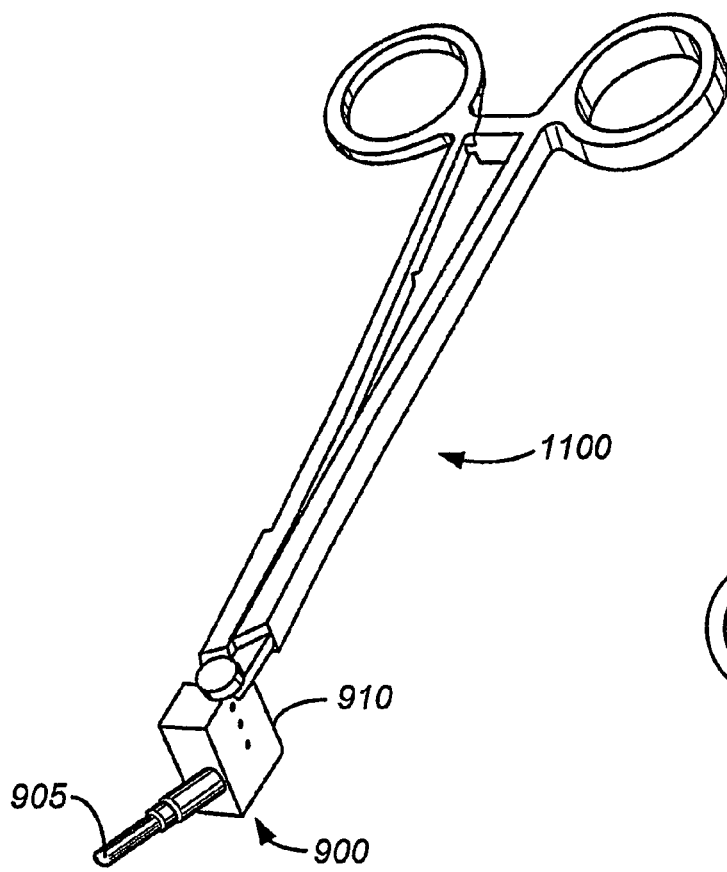
FIGS. 17A-C are views of a tool for implanting the measurement tool of the invention.
Figure 17B:
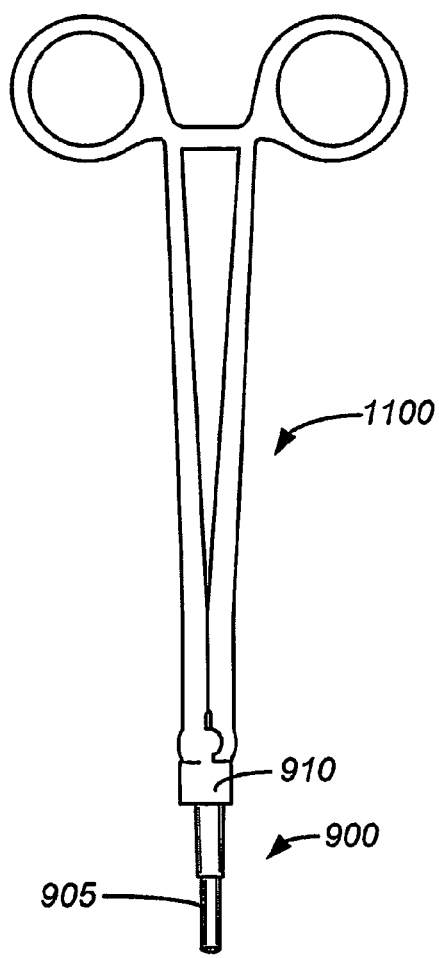
Figure 17C:
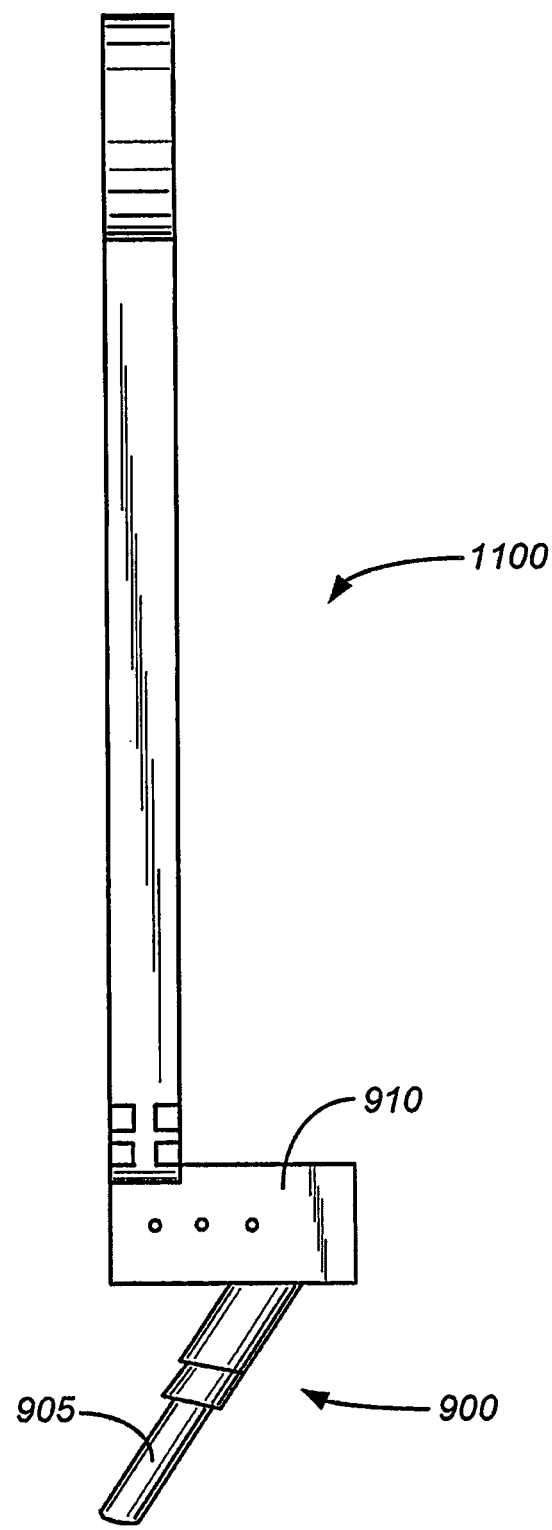

In the embodiment shown in FIG. 17 the component selection tool 900 of FIG. 15 is combined with a delivery tool 1000 such as a pair of forceps with a configured distal end for engaging the component selection tool 900. As will be appreciated by those skilled in the art, any instrument resembling a pair of pincers or tongs, used for grasping, manipulating, or extracting, that is adapted at an end to engage the component selection instrument would be suitable. Adapted forceps are depicted for purposes of illustration. FIG. 17A illustrates a perspective view of the forceps 1000 engaging the component selection instrument 900. FIG. 17B illustrates the forceps 1000 engaging the component selection instrument 900 from a first planar view, while FIG. 17c illustrates the forceps 1000 engaging the component selection instrument 900 from a second planar view. Although these embodiments illustrated the component selection instrument 900 and the forceps engaging the instrument as two separate components, as will be appreciated by those skilled in the art an integrally formed configuration could be used without departing from the scope of the invention.

Figure 18A:
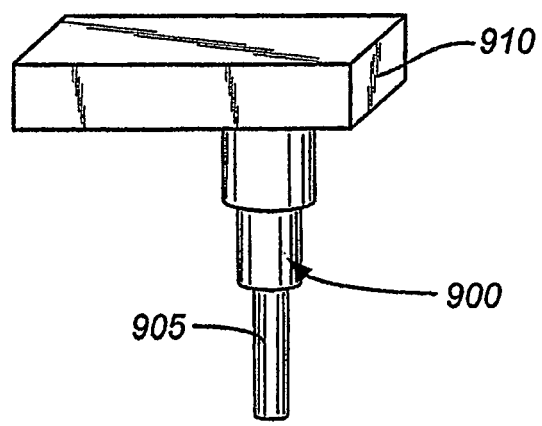
FIGS. 18A-D illustrate a measurement tool of the invention along with guides used with the measuring tool to assess the size and angle of the device to be implanted.
Figure 18B:
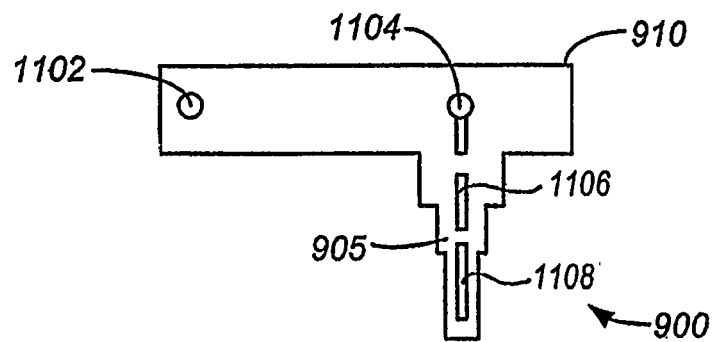
Figure 18C:
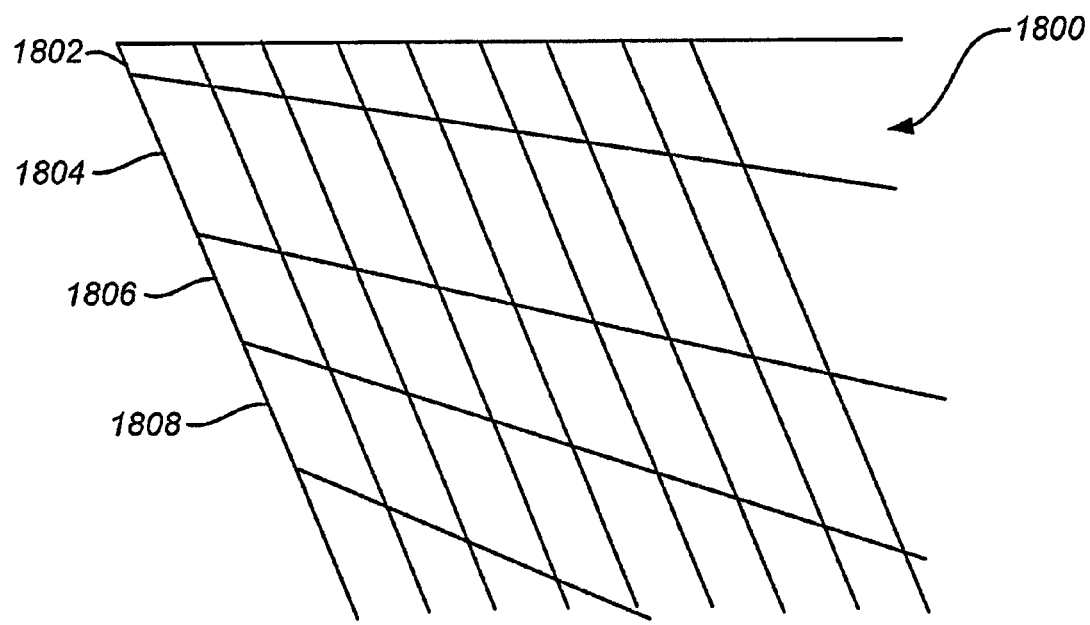
Figure 18D:
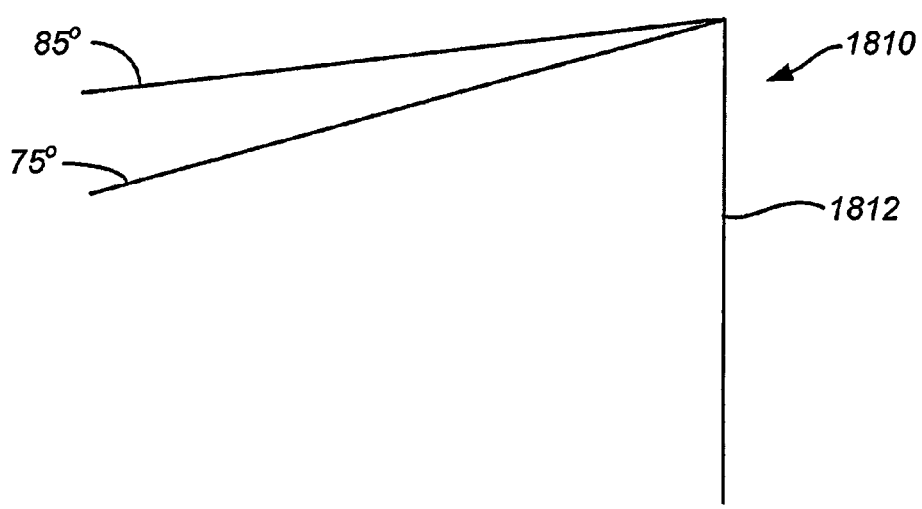

FIG. 18A illustrates a perspective view of a component selection tool 1100. The component selection tool 1100 has a head 910 and a stem 905 configured differently than the component selection tool 900 of FIG. 14. A variety of radiopaque markers 1102, 1104, 1106, 1108 are provided as shown in FIG. 18B. FIG. 18C illustrates a gauge 1800 for use in determining cephalad arm length from an A/P view. The gauge 1800 is calibrated to provide an indication of a known distance 1802 of the markers in the component selection instrument. From that point, a small region 1804, medium region 1806, and large region 1808 is also marked. The calibration gauge 1800 can also be used in a similar manner with other joints. Turning now to FIG. 18D another gauge 1810 is provided. A first line 1812 is oriented along a component selection instrument cephalad stem orientation line. From that point, the angle of the stem can be determined, e.g. 75°, 85°.

Figure 19A:
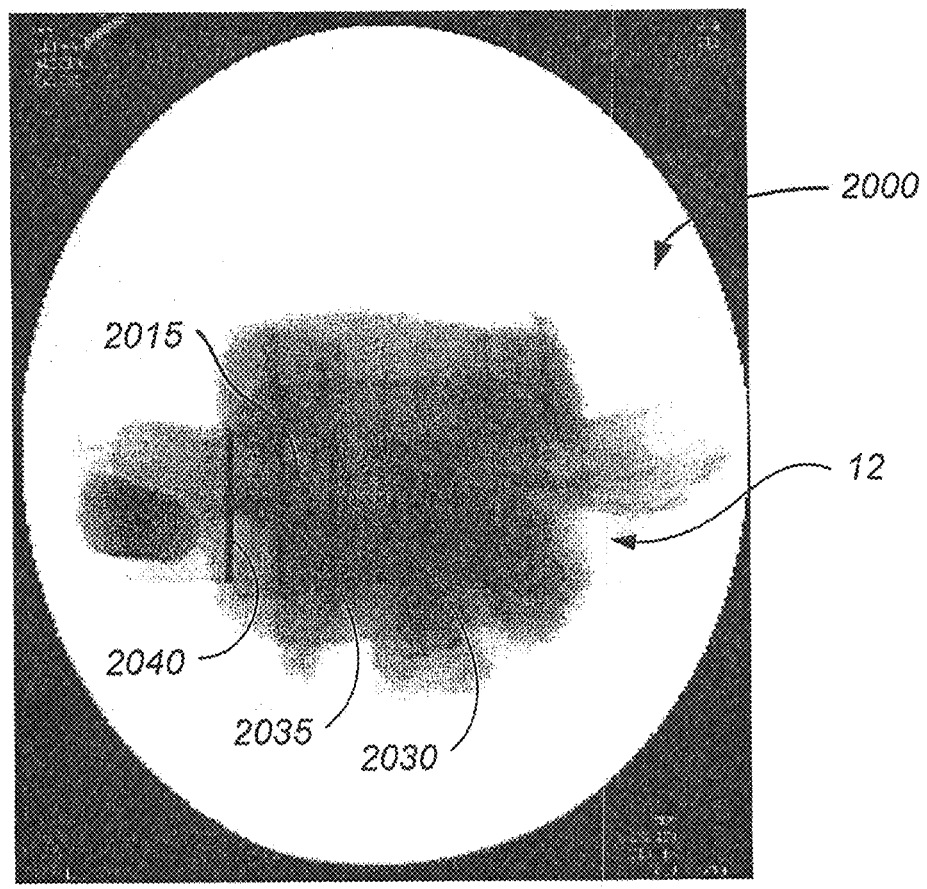
FIG. 19A illustrates an image taken of a section of spine with the measurement tool incorporated therein to provide radiopaque markers.
Figure 19B:
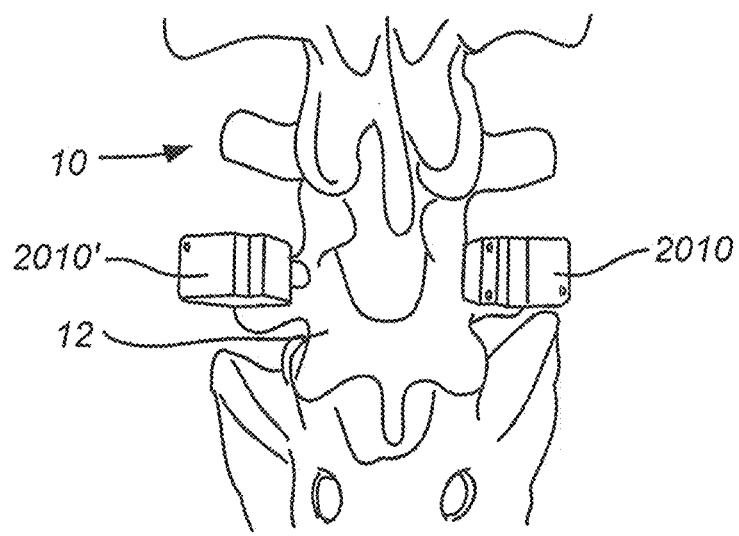
FIG. 19B illustrates a spine having two measurement tools associated therewith.

For example, FIG. 19A depicts an A/P radiographic image 2000 of one embodiment of a component selection instrument 2010 positioned within a pedicle of a targeted vertebral body. In this embodiment, the ball 2015 is positioned between two radiopaque markers 2030, 2035 nearest marker 2035. FIG. 19B is an image of a spinal column with two component selection instruments 2010, 2010' placed therein.

Figure 20A:
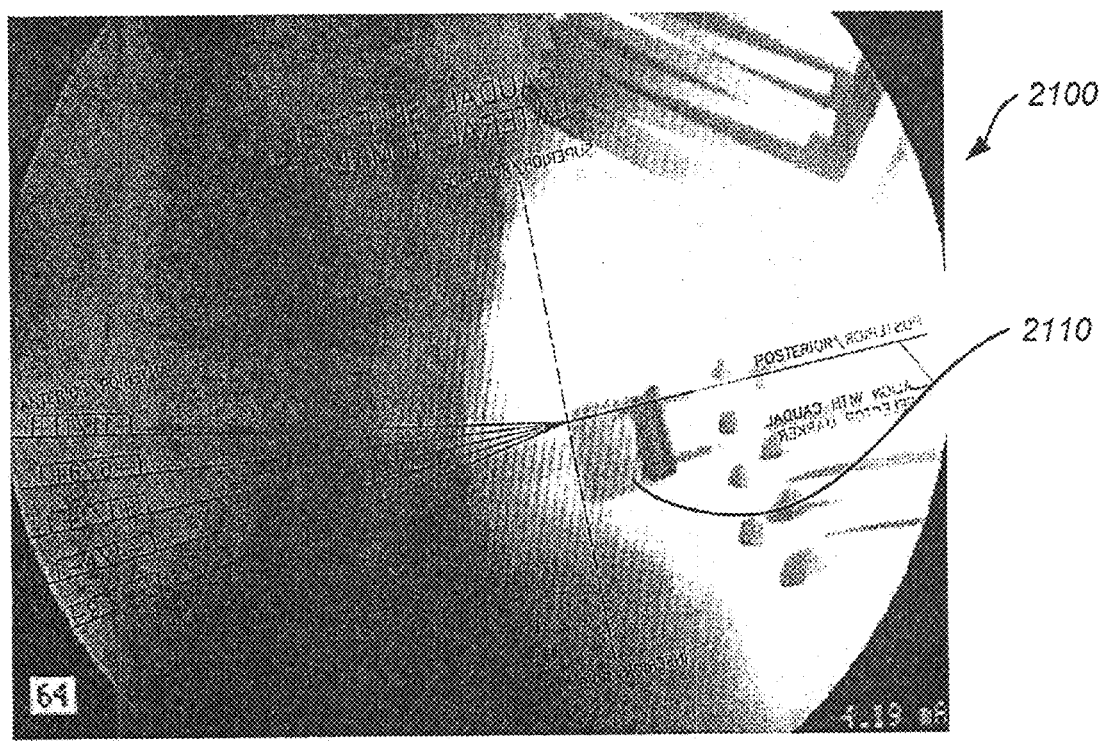
FIG. 20A illustrates a radiological image of a caudad selection tool in combination with a sizing template.
Figure 20B:
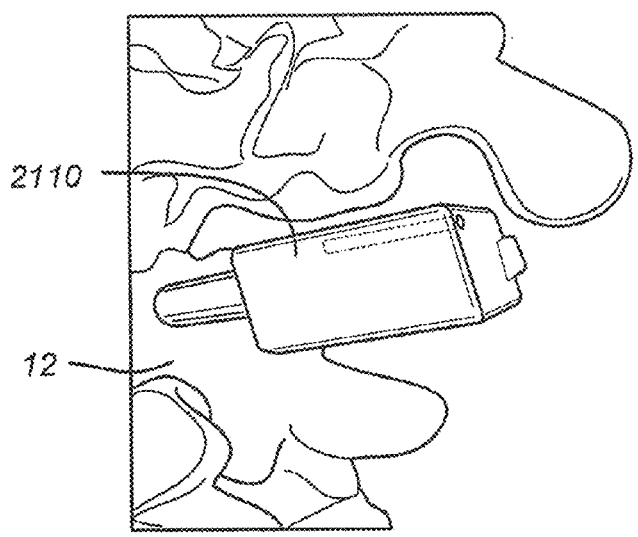
FIG. 20B illustrates a portion of the spine with the measurement tools extending therefrom.

FIG. 20A is a lateral radiographic image 2100 of a spine with a component selection instrument 2110 associated therewith. A caudal selector lateral template is used in conjunction with the image to assess the optimal orientation of the caudad selector. Values from −9 to +11 are indicated 2112. This assists in denoting the desired implant component (corresponding to that anatomical orientation of the vertebral body) which accommodates an axial angle (relative to the sagittal plane). In a desired embodiment, a single A/P view can be utilized to characterize the pedicle of a single targeted vertebral body. In a more desirable embodiment, a single A/P view can be utilized to characterize both pedicles of a single targeted vertebral body, each pedicle of which will incorporate a single component selector instrument. In a most desirable embodiment, a single A/P view can be utilized to characterize the pedicles of multiple targeted vertebral bodies (adjacent or non-adjacent), with the pedicles of the vertebral bodies each incorporating a single component selector instrument. As will be appreciated by those skilled in the art, additional views from the same or different perspectives can also be used without departing from the scope of the invention, including slices taken using an MRI. FIG. 20B illustrates an image of a portion of a spine model having a component selection instrument 2110 associated therewith.

Figure 21:
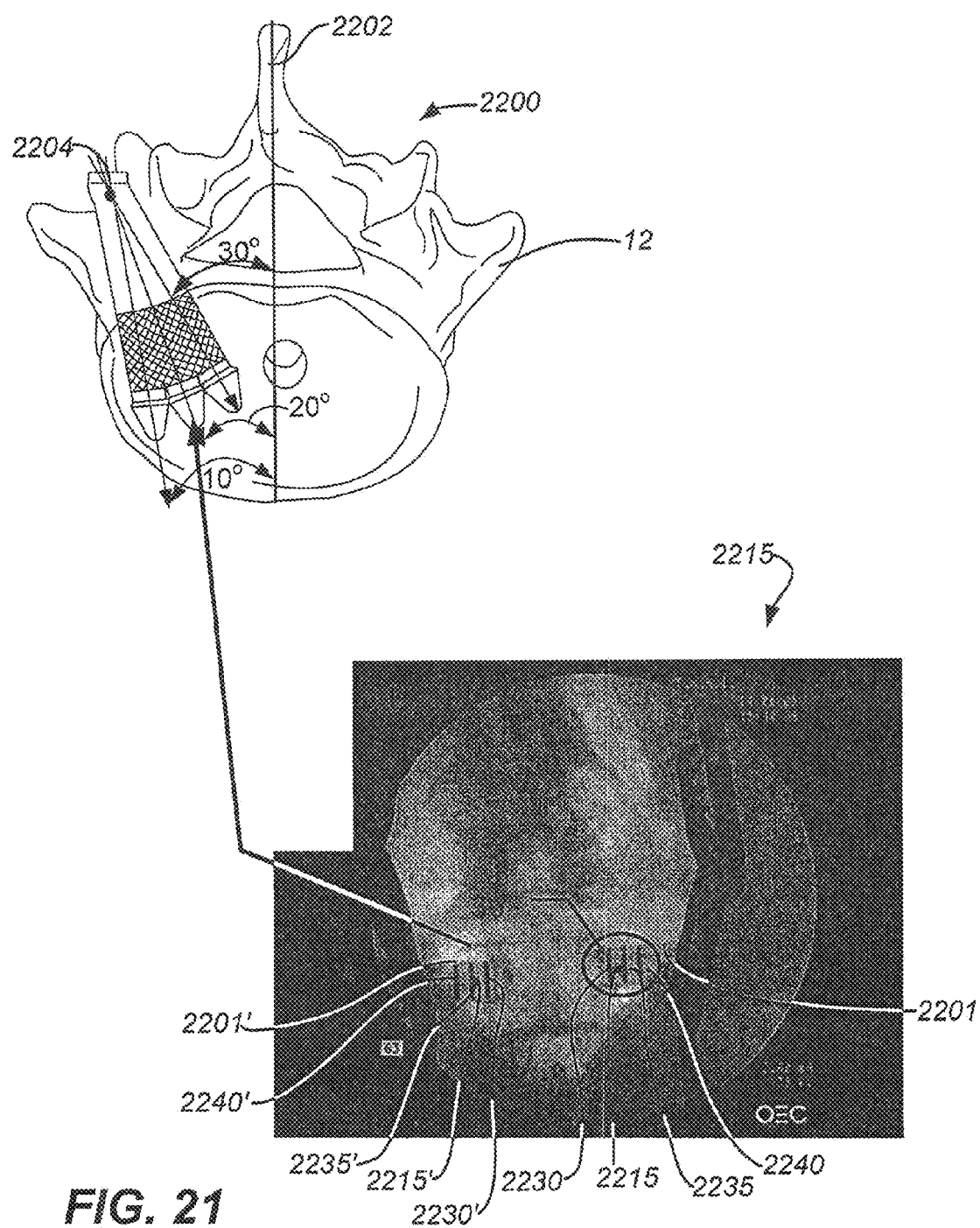
FIG. 21 illustrates a superior view of a vertebral body with a measurement tool associated therewith and a radiological image of the measurement tool within the spine.

Turning to FIG. 21 an image of a vertebral body from a superior position 2200 is illustrated having a midline 2202. Three possible orientations 2206 of a stem 2204 are illustrated at, e.g., 10°, 20° and 30°. A radiological image 2210 from a posterior view illustrates the lines and circles of the markers corresponding to, in this instance a location of the circular marker between the innermost two marker lines which indicates a 30° angle to the midline 2202. In this image, two component selection instruments are positioned within the vertebral body for selecting the caudad facet joint. The axial plane angles are measured for selecting a caudad facet joint. In selecting the optimal angle, the physician locates the ball shaped marker 2215, 2215' of the component selection instrument. Due to the orientation of the marker 2215, 2215' to a second set of markers 2230, 2235, 2240, which appear as vertical lines in the image, in the two dimensional plane the marker 2215 appears to be located between the lines formed by markers 2230, 2235, 2240. Each of the markers 2230, 2235, 2240 corresponds to an angle such that identifying the angle using the component selection instrument enables the physician to select an implant, such as a caudad facet joint, having an angled orientation that best matches the anatomy of the patient. As shown in FIG. 21 the image depicted has two component selection instruments 2201, 2201'. The first component selection instrument 2201 has marker 2215 between two markers positioned nearest the midline of the spine. The marker nearest the midline of the spine corresponds to a 30° angle, thus the facet joint selected for the joint measured by component selection instrument 2201 is a 30° facet joint device. The second component selection instrument 2201' has marker 2215 positioned partially over the middle vertical marker. The middle vertical marker corresponds to a 20° angle, thus the facet joint selected for the joint measured by component selection instrument 2201' is a 20° facet joint device.

Figure 22:
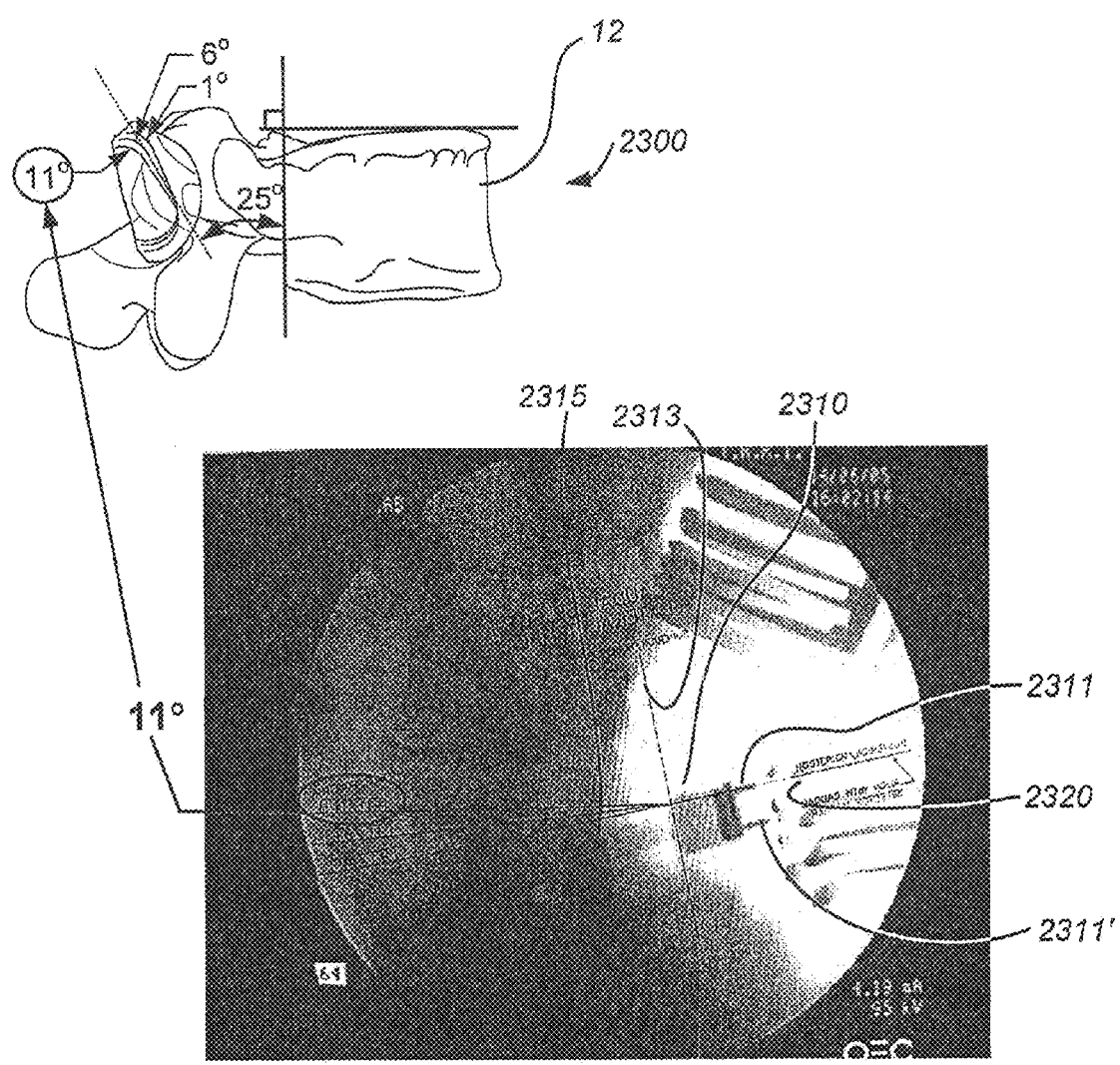
FIG. 22 illustrates a side view of vertebral body with two measurement tools associated therewith and a radiological image of the tool within the spine.

FIG. 22 illustrates another image of a vertebral body from a side view 2300. The spinous process 22 is apparent as well as the superior facet joint 32. In viewing the corresponding radiographic image from the side of a spine having a two component selector instruments associated therewith along with the template, the image indicates that the size component would correspond to 11°. The ball marker 2315 appears as a ball near the spine 12 in the image. In the component selection instrument 2301 of this device, two different types of markers have been used as described above, smooth profiled wire, and turned wire with a curved profile. The first marker 2311 of the first component selection instrument is a smooth wire, the second marker 2311' of the second component selection instrument is a turned marker. Thus enabling the physician to associate two component selection instruments within the spine and to determine, based on the type of marker 2311, 2311' the location of within the spine that corresponds to the measurement. When measuring the sagittal plane angles using an image taken from this orientation, a template is lined up with the posterior wire 2320 and the distal face of the head 2310 at an axis 2313. On the opposing side of the axis 2313 a series of lines can be measured to correspond to the appropriate angle of the device to be implanted. Three angle lines are depicted, +1, +6, +11. In selecting the angle, the line that corresponds to the top surface of the vertebral body associated with the component selection instrument is selected. In the image provided, the selection corresponds to the +11.

If desired, the implantable spinal components can be selected from a group of modular components having dimensions and sizes which directly correspond to the various measurements determined from the component selection instrument (or can be marked with similar markings on the component and component selection/template). For example, the vertical radiopaque markers on the component selection instrument could be marked 10°, 20° and 30° (which would desirably be visible on the radiographic image), and similar markings (10°, 20° and 30°) could appear on the corresponding modular components (in this embodiment, the modular stems) of the artificial facet joints. Similarly, the template could incorporate markings for −4°, 9°, 1°, 6° and 11°. and similar markings (−4°, −9°, 1°, 6°and 11°) could appear on the corresponding modular components (in this embodiment, the modular caudad cups) of the artificial facet joints.

In a similar manner, a single lateral image can desirably be utilized to determine the necessary characteristics of the targeted vertebral body(ies) as well. For a lateral view, the component selection instrument incorporates a single horizontal marker, which can be seen on the radiographic image. Desirably, a clear or translucent template, such as described above with respect to FIG. 22, can be placed over the radiographic image (or against the monitor screen, in the case of real-time fluoroscopy), and the angle between the upper endplate (or other desired anatomical feature) and the marker can be assessed visually with the template. Desirably, the physician can then choose the implant component which corresponds to that measurement. As with the previously described views, in a desired embodiment, a single lateral view can be utilized to characterize the pedicle of a single targeted vertebral body. In a more desirable embodiment, a single lateral view can be utilized to characterize both pedicles of a single targeted vertebral body, each pedicle of which will incorporate a single component selection instrument. In a most desirable embodiment, a single lateral view can be utilized to characterize the pedicles of multiple targeted vertebral bodies (adjacent or non-adjacent), with the pedicles of the vertebral bodies each incorporating a single component selection instrument.

Desirably, the component selector instrument(s) will, when properly positioned, allow the physician to take a single lateral radiographic image, and/or a single anterior/posterior (A/P) image, and determine the necessary characteristics of the targeted vertebral body(ies) to accurately choose components and construct a facet replacement construct with minimal time, effort and radiation exposure to the patient. Moreover, because in various embodiments the entirety of the component selection instrument is contained within the wound, and desirably does not extend out of the wound opening, the disclosed measurement system significantly reduces the opportunity for the radiographic imaging apparatus to contact objects in the sterile field. If desired, one or more component selection instruments could be implanted, and then the surgical wound covered and/or closed, and imaging to occur, with no reduction in the ability of the apparatus to measure the anatomical characteristics of the surgical site. In addition, because the disclosed anatomical measurement system determines the anatomical measurements through comparisons of angular relationships and/or known distances, the disclosed system is desirably immune to the effects of magnification and/or distortion of the radiographic images (which can include unknown magnification of the radiographic images, varying monitor and/or print-out size, and/or inaccurate and/or out-of-date calibration of the imaging equipment itself).

In use, a physician can perform a surgical procedure (including surgical procedures that result in destabilization and/or damage to the spinal column and/or facet joints), and then prepare the surgical site for implantation of a facet joint replacement device. Desirably, the surgeon will drill a hole into each pedicle of the targeted vertebral body(ies), and then insert a component selection instrument into the hole. To reduce the size and "footprint" of the component selection instrument, each component selection instrument desirably incorporates a reduced-width gripping section, which facilitates gripping and manipulation of the component selection instrument using a pair of surgical clamps or forceps, but allows the clamp to be removed during visualization, if desired, (as well as to reduce the size and "footprint" of the component selection instrument within the wound). Desirably, the surgeon will visually align the component selection instrument (using, for example, the lateral edge of the body, etc.) with the spinous process of the targeted vertebral body, or other desired anatomical landmark. One the radiographic images (A/P and lateral) have been taken, the component selection instruments can be removed and implantation of the desired facet joint replacement components can be accomplished.

With respect to the measurement and characterization of the cephalad components for a facet joint replacement artificial facet joints, a similar component selection instrument can be utilized. However, because the cephalad components can be significantly different in form and/or function from the caudad components, a component selection instrument best suited for measurement and characterization of cephalad components may measure significantly different anatomical characteristics of the cephalad and/or caudad vertebral bodies.

The radiolucent tool with radiopaque markers allows a surgeon to determine which angles are appropriate for the artificial orthopedic devices being inserted, such as the artificial caudad facet joint and the artificial cephalad facet joint described above. By using imaging and referencing the integral radiopaque marker in the instrument against anatomical references of a patient, the surgeon can determine the appropriate angle of device to use to achieve optimal results for the patient. The device can also be adjusted in situ to reference anatomical landmarks through direct visual means, or to allow the user to determine the most appropriate angle for viewing.

Figure 23:
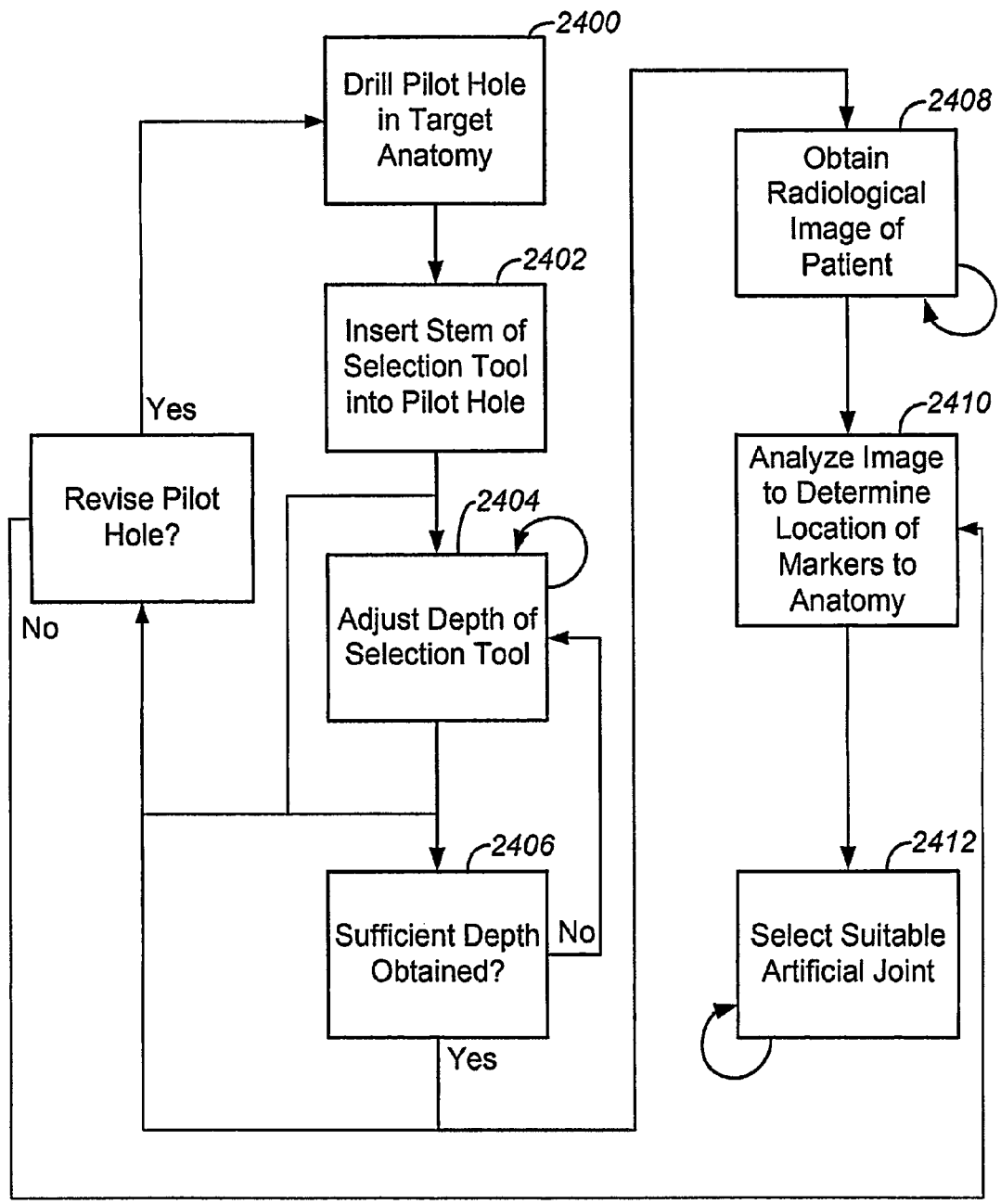
FIG. 23 is a flow chart illustrating method steps for determining the size of an artificial facet joint using the tools of the invention.

FIG. 23 illustrates a flow chart of a method for using the component selection tool. Initially, target anatomy is accessed, preferably in a minimally invasive fashion. A pilot hole is drilled 2400, e.g. in the target vertebral body. The stem of the component selection instrument is then inserted into the pilot hole 2402. Where the component selection tool has is stepped or telescoped, or has a variable diameter along its length, the depth to which the component selection tool may be inserted into the pilot hole may be effected, as discussed above. The depth at which the component selection tool is inserted can be adjusted 2404, if desired. Once sufficient depth is obtained 2406, a radiologic image is taken of the patient 2408 using known techniques. The image is then analyzed 2410 to determine the location of the markers in the component selection instrument relative to the target anatomy. At any point, the pilot hole can be revised 2411 to provide a pilot hole with a larger diameter after which another image can be taken (thus repeating step 2408). Based on one or more images taken, a suitable artificial joint can be selected 2412 for the target anatomy.

While preferred embodiments of the invention have been illustrated and described, it will be appreciated that various changes can be made therein without departing from the spirit and scope of the invention. Moreover, while the present inventions have been described for use with a modular artificial joint system, it should be understood that the present inventions have utility in conjunction with the measurement and placement of other artificial joint systems, including single component, multi-component and custom-made artificial joints, with varying results. Further, the trialing system described herein can comprise single or multi-component tools and devices.

What is claimed is:

1. A surgical method comprising:
   drilling a hole in a vertebral body;
   inserting a component selection instrument in the hole, wherein the component selection instrument includes at least one radiopaque marker;
   taking an image of the component selection instrument;
   analyzing image to determine location of the at least one radiopaque marker; and
   selecting an implant based on the image analysis.

2. The surgical method of claim 1, further comprising providing the implant into the revised hole, the implant is an artificial joint.

3. The surgical method of claim 2, wherein the artificial joint comprises a facet joint implant.

4. The surgical method of claim 1, wherein the component selection instrument comprises a stem and a head.

5. The surgical method of claim 4, wherein the stem and the head are formed of radiolucent materials.

6. The surgical method of claim 4, wherein the stem comprises a distal section, a central section and a proximal section, wherein the distal section has a diameter less than the central section, and the central section has a diameter less than the proximal section.

7. The surgical method of claim 4, wherein the head comprises one or more radiopaque markers.

8. The surgical method of claim 7, wherein the head comprises at least two radiopaque markers parallel to one another.

9. The surgical method of claim 8, further comprises at least two additional radiopaque markers that are transverse to the at least two radiopaque markers in parallel.

10. A surgical method comprising:
    drilling a hole in a vertebral body;
    inserting a component selection instrument in the hole, wherein the component selection instrument includes at least one radiopaque marker;
    taking an image of the component selection instrument;
    revising the size of the hole to have a larger diameter;
    analyzing image to determine location of the at least one radiopaque markers; and
    selecting an implant based on the image analysis.

11. The surgical method of claim 10, further comprising providing the implant into the revised hole, the implant is an artificial joint.

12. The surgical method of claim 11, wherein the artificial joint comprises a facet joint implant.

13. The surgical method of claim 10, wherein the component selection instrument comprises a stem and a head.

14. The surgical method of claim 13, wherein the stem and the head are formed of radiolucent materials.

15. The surgical method of claim 13, wherein the stem comprises a distal section, a central section and a proximal section, wherein the distal section has a diameter less than the central section, and the central section has a diameter less than the proximal section.

16. The surgical method of claim 13, wherein the head comprises one or more radiopaque markers.

17. The surgical method of claim 16, wherein the head comprises at least two radiopaque markers parallel to one another.

18. The surgical method of claim 17, further comprises at least two additional radiopaque markers that are transverse to the at least two radiopaque markers in parallel.

19. The surgical method of claim 13, wherein the stem is formed of material having a different radiopacity from the head.

20. The surgical method of claim 13, wherein the stem is formed of a radiolucent polymer.

* * * * *